United States Patent
Reule et al.

(10) Patent No.: US 10,695,756 B2
(45) Date of Patent: Jun. 30, 2020

(54) METAL-LOADED ZEOLITE CATALYSTS FOR THE HALOGEN-FREE CONVERSION OF DIMETHYL ETHER TO METHYL ACETATE

(71) Applicants: Allen Artur Carl Reule, Alberta (CA); Natalia Semagina, Alberta (CA); Esteban Chornet, Sherbrooke (CA)

(72) Inventors: Allen Artur Carl Reule, Alberta (CA); Natalia Semagina, Alberta (CA); Esteban Chornet, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 261 days.

(21) Appl. No.: 15/168,972

(22) Filed: May 31, 2016

(65) Prior Publication Data
US 2017/0072388 A1    Mar. 16, 2017

Related U.S. Application Data

(60) Provisional application No. 62/314,624, filed on Mar. 29, 2016, provisional application No. 62/174,617, filed on Jun. 12, 2015.

(51) Int. Cl.
| | | |
|---|---|---|
| *B01J 29/06* | (2006.01) | |
| *B01J 29/24* | (2006.01) | |
| *C07C 67/37* | (2006.01) | |
| *B01J 29/90* | (2006.01) | |
| *B01J 38/10* | (2006.01) | |
| *B01J 29/22* | (2006.01) | |
| *B01J 29/40* | (2006.01) | |
| *B01J 29/44* | (2006.01) | |
| *B01J 29/46* | (2006.01) | |
| *B01J 29/035* | (2006.01) | |
| *B01J 37/30* | (2006.01) | |
| *B01J 29/18* | (2006.01) | |
| *B01J 37/14* | (2006.01) | |
| *B01J 37/18* | (2006.01) | |

(52) U.S. Cl.
CPC .......... *B01J 29/24* (2013.01); *B01J 29/0354* (2013.01); *B01J 29/0356* (2013.01); *B01J 29/185* (2013.01); *B01J 29/22* (2013.01); *B01J 29/405* (2013.01); *B01J 29/44* (2013.01); *B01J 29/46* (2013.01); *B01J 29/90* (2013.01); *B01J 37/14* (2013.01); *B01J 37/18* (2013.01); *B01J 37/30* (2013.01); *B01J 38/10* (2013.01); *C07C 67/37* (2013.01); *B01J 2229/16* (2013.01); *B01J 2229/183* (2013.01); *B01J 2229/186* (2013.01); *B01J 2229/37* (2013.01)

(58) Field of Classification Search
CPC . B01J 29/405; B01J 29/44; B01J 29/46; B01J 29/22; B01J 29/24; B01J 29/185; B01J 29/0354; B01J 29/0356; B01J 2229/186; B01J 37/14; B01J 37/18; B01J 37/30

USPC .............................................. 502/74, 77, 78
See application file for complete search history.

(56) References Cited

U.S. PATENT DOCUMENTS

| | | | | |
|---|---|---|---|---|
| 6,255,527 B1* | 7/2001 | Muskett | ..................... | B01J 3/04 562/519 |
| 7,976,697 B2* | 7/2011 | Krishnamoorthy | .... | B01J 29/068 208/120.01 |
| 8,071,828 B2* | 12/2011 | Cao | ........................... | C07C 2/66 585/319 |
| 8,329,606 B2 | 12/2012 | Becker et al. | | |
| 8,394,983 B2 | 3/2013 | Ditzel et al. | | |
| 8,431,732 B2 | 4/2013 | Armitage et al. | | |
| 9,505,702 B2 | 11/2016 | Becker et al. | | |
| 9,505,703 B2 | 11/2016 | Ditzel et al. | | |
| 2005/0096211 A1* | 5/2005 | Takeda | ..................... | B01J 23/06 502/66 |
| 2008/0230017 A1* | 9/2008 | Kobayashi | ............... | B01J 23/60 123/3 |
| 2011/0085944 A1* | 4/2011 | Rolllins | ................. | B01J 29/005 422/211 |
| 2011/0098513 A1* | 4/2011 | Weiner | ..................... | B01J 29/08 568/698 |
| 2011/0190556 A1* | 8/2011 | Levin | ..................... | B01J 29/064 585/251 |
| 2012/0053382 A1* | 3/2012 | Wang | ..................... | B01J 29/068 585/450 |

(Continued)

FOREIGN PATENT DOCUMENTS

| | | |
|---|---|---|
| WO | WO 2009/077743 | 6/2009 |
| WO | WO 2010/061169 | 6/2010 |

(Continued)

OTHER PUBLICATIONS

Inui, et al., Sekiyu Gakkaishi, vol. 28, No. 3, pp. 225-233 (1985).
Denise, et al., Applied Catalysis, vol. 27, pp. 107-116 (1986).
Arenamnart, et al., Int. J. Appl. Sci. Eng., vol. 4, No. 1, pp. 21-32 (2006).
Khandan, et al., Catal. Lett., vol. 129, pp. 111-118 (Nov. 26, 2008).
Wang, et al., Fuel, vol. 109, pp. 54-60 (Sep. 24, 2012).
Lu, et al., Catalysis Today, vol. 232, pp. 22-26 (Nov. 12, 2013).
Li, et al., Applied Catalysis A: General, vol. 425, pp. 155-160 (Jan. 21, 2014).

(Continued)

*Primary Examiner* — Elizabeth D Wood
(74) *Attorney, Agent, or Firm* — Raymond J. Lillie

(57) ABSTRACT

A catalyst for the carbonylation of dimethyl ether to methyl acetate. The catalyst comprises a zeolite, such as a mordenite zeolite, at least one Group IB metal, such as copper, and/or at least one Group VIII metal, such as iron, and at least one Group IIB metal, such as zinc. Such a catalyst with combined metals provides enhanced catalytic activity, improved stability, and improved selectivity to methyl acetate, and does not require a halogen promoter, as compared to a metal-free or copper only zeolite.

5 Claims, 24 Drawing Sheets

(56) References Cited

U.S. PATENT DOCUMENTS

2013/0102809 A1* 4/2013 Le Berre ................ C07C 51/12
562/519

FOREIGN PATENT DOCUMENTS

| WO | WO 2010/067043 | 6/2010 |
|----|----------------|--------|
| WO | WO 2014/135663 | 9/2014 |

OTHER PUBLICATIONS

Cheung, et al. Angew.Chem. Int., vol. 45, pp. 1617-1620 (2006).
Cheung, et al., Journal of Catalysis, Vo. 245. pp. 110-123 (available online Oct. 27, 2006).
Bhan, et al., J. Am. Chem. Soc., vol. 129, pp. 4919-4924 (2007).
Boronat, et al., J. Am. Chem. Soc., vol. 130, pp. 16316-16323 (2008).
Liu, et al., Catal. Lett., vol. 139, pp. 33-37 (2010).
Li, et al., J. Phys. Chem., vol. 117, pp. 5840-5847 (Mar. 1, 2013).
Dusselier, et al., Chem. Rev., vol. 118, pp. 5265-5329 (May 10, 2018).

* cited by examiner

METAL-LOADED ZEOLITE CATALYSTS FOR THE HALOGEN-FREE CONVERSION OF DIMETHYL ETHER TO METHYL ACETATE

This application claims priority based on Provisional Application Ser. No. 62/174,617, filed Jun. 12, 2015 and Provisional Application Ser. No. 62/314,624, filed Mar. 29, 2016, the contents of which are incorporated by reference in their entireties.

This invention relates to catalysts used in the conversion of dimethyl ether to methyl acetate, in which dimethyl ether is reacted with carbon monoxide to produce methyl acetate. More particularly, this invention relates to catalysts used in the conversion of dimethyl ether to methyl acetate, wherein the catalyst comprises (i) a zeolite; (ii) at least one Group IIB metal; and (iii) at least one metal selected from the group consisting of Group IB metals and Group VIII metals. Although Applicants do not intend to be limited thereby, such catalysts and the reactions catalyzed by such catalysts in general are free of iodine, iodides, and other halogens or halogen-containing compounds.

Many catalysts used in the conversion of dimethyl ether to methyl acetate are based on zeolites, such as mordenite zeolites. Many of these catalysts may have high activity but deactivate quite quickly due to the formation of heavy organic compounds in the pores and channels of the zeolite framework, which blocks access of the reactants to active sites. As a result, these catalysts do not sustain a high rate of methyl acetate production.

In addition, when these catalysts begin to deactivate, such as, for example, by the formation of coke deposits on the catalyst, the selectivity toward methyl acetate also declines with time of catalyst exposure to the reactants. Selectivity during the course of reaction shifts to favor the production of methanol and other oxygenates and hydrocarbons until the catalyst is deactivated completely and no longer fosters the conversion of dimethyl ether. (See, for example, Liu, et al., *Catalysis Letters*, Vol. 139, pgs. 33-37 (2010); Xue, et al., *Ind. Eng. Chem.*, Vol. 52, pgs. 11510-11515 (2013); Cheung, et al., *Anqew. Chem. Int. Edit.*, Vol. 45, pgs. 1617-1620 (2006); Xue, et al., *Catal. Commun.*, Vol. 37, pgs. 75-79 (2013); Liu, et al., *Chinese J. Catal.*, Vol. 31, pgs. 729-738 (2010); and Zhang, et al., *Chin. J. Chem. Phys.*, Vol. 26, pgs. 77-82 (2013)).

U.S. Pat. No. 8,431,732 discloses a process for the production of methyl acetate via carbonylation of dimethyl ether (DME) or dimethyl carbonate over a Group IB loaded mordenite catalyst, more specifically, copper, silver, or gold or mixtures thereof. The carbonylation reactions were performed at a pressure of 70 bar and a temperature of 300° C. using a mixture of carbon monoxide (CO), hydrogen ($H_2$). and DME with a molar ratio of CO/$H_2$/DME of 72/18/10. The reaction results showed a high peak selectivity towards the desired methyl acetate product, which decreased slightly as the catalyst deactivated. One noted by-product of the reaction was acetic acid. These catalysts have the disadvantage of using silver, a more expensive metal as compared to the metals used in the present invention. These reactions also were carried out with an excessive amount of $H_2$ in the feed, which is not required for stoichiometric conversion.

PCT Application No. WO 2010/061169 discloses a process for the production of methyl acetate via carbonylation of dimethyl ether over a mordenite catalyst loaded with at least one metal selected from copper, silver, gold, nickel, iridium, rhodium, platinum, palladium, or cobalt with preference given to copper and silver. The reactions were carried out at 70 bar pressure and a temperature of 300° C. Inlet reactant gas conditions varied, but contained 18 mol % to 29 mol % $H_2$. The DME concentration was varied in the feed but never was more than 5 mol %. Selectivity towards methyl acetate and catalyst stability were improved by the addition of methyl acetate (the product) into the feed gas at quantities not exceeding 5 mol %. Without the addition of methyl acetate into the reactant gas, catalyst performance was similar to that as described in U.S. Pat. No. 8,431,732. The disadvantage of these catalysts is that they are based predominantly on using copper and silver, the latter of which is a comparatively expensive metal. The reaction also is carried out at high temperature and pressure with large amounts of $H_2$.

PCT Application No. WO 2009/077743 discloses a process for the production of methyl acetate and/or acetic acid via the carbonylation of feedstocks such as dimethyl ether, methanol, or dimethyl carbonate in the presence of a mordenite zeolite loaded with Group IB metals, more specifically, copper, silver, and gold. The carbonylation reactions were performed at a pressure of 70 bar and a temperature of 300° C. using a reactant gas with a molar ratio of CO/$H_2$/DME of 72/18/10 at a GHSV of 4000 $h^{-1}$. The reaction results showed a high peak selectivity towards the desired product methyl acetate (approximately 93%), but this decreased as the catalyst deactivated.

PCT Application No. WO 2014/135663 discloses a process for the production of methyl acetate via carbonylation of dimethyl ether over a mordenite catalyst loaded with at least one metal selected from copper, silver, nickel, iridium, rhodium, platinum, palladium, and cobalt. The reactions were carried out at pressures between 20 to 80 bar and temperatures between 240 to 320° C. The reactant gas contained a molar excess of $H_2$ relative to CO so as to improve catalyst stability. Specifically, no example is provided with a $H_2$ content less than 17.5 mol % in the reactant feed gas. There also may be present some small amount of the halide or iodide, i.e., less than 500 ppm with preference given to less than 100 ppm. While the reaction selectivity appears to be high, i.e., 97-98%, such selectivity is at the expense of using excessive amounts of $H_2$ in the feed and possibly the use of the halide.

U.S. Pat. No. 8,329,606, discloses a process for the in situ regeneration of a zeolite catalyst used in a carbonylation process for the production of at least one of methyl acetate and acetic acid. In this process the regeneration is carried out in a pressure range of 1 to 80 bar and a temperature range of 300 to 500° C. using a hydrogen and carbon monoxide gas mixture. The catalyst is regenerated under these conditions for 10 to 50 hours. The catalyst is shown to have its activity restored at least partially without negligible effect on the selectivity to the desired product after regeneration. The regeneration procedure was shown to work multiple times on the same catalyst.

PCT Application No. WO 2010/067043 discloses a process for the carbonylation of either dimethyl ether or methanol with carbon monoxide to produce one of either methyl acetate or acetic acid. This is done in the presence of a mordenite zeolite loaded with at least one of silver and copper with an inorganic oxide binder. The carbonylation reaction was carried out with a large amount of hydrogen present; specifically, the molar ratio of carbon monoxide to hydrogen was in the range 1:3 to 15:1. The inlet reactant gas consisted of CO, $H_2$, and DME at a molar ratio of CO/$H_2$/DME of 72/18/10. Reactions were performed at a total pressure of 70 bar and a temperature of 300° C. at a GHSV of 4275 h$^{-1}$. Peak selectivity towards methyl acetate was reported at 96% with small amounts of acetic acid as the primary by-product.

It is an object of the present invention to provide a catalyst for the halide-free conversion of dimethyl ether to methyl acetate that maintains a high selectivity toward methyl acetate during the course of the reaction, even as the catalyst begins to deactivate.

It is another object of the present invention to provide a catalyst for the halide-free conversion of dimethyl ether to methyl acetate in which little or no acetic acid is produced as a by-product.

Thus, in accordance with an aspect of the present invention, there is provided a catalyst for the carbonylation of dimethyl ether to produce methyl acetate, thereby carbonylating the dimethyl ether. The catalyst comprises (i) a zeolite; (ii) at least one Group BB metal; and (iii) at least one metal selected from the group consisting of Group IB metals and Group VIII metals.

In a non-limiting embodiment, the zeolite is selected from the group consisting of mordenite zeolites, zeolite Beta, ferrierite, zeolite Y, ZSM-5, ZSM-23, ZSM-35, and ZSM-57. The zeolites may be commercial, as received, zeolites, or maybe hierarchical zeolites.

In another non-limiting embodiment, the zeolite is a mordenite zeolite.

In a non-limiting embodiment, the mordenite zeolite has a Si/Al ratio of from about 5:1 to about 90:1. In another non-limiting embodiment, the mordenite zeolite has a Si/Al ratio of from about 5:1 to about 50:1.

The Group IIB, Group IB, and Group VIII metals that may be contained in the catalyst of the present invention are those listed in the old IUPAC groups nomenclature of the Periodic Table of the Elements, IUPAC 1990. Thus, the Group IIB metals are zinc, cadmium, mercury and copernicium. The Group IB metals are copper, silver, gold, and roentgenium. The Group VIII metals which may be contained in the catalyst of the present invention are iron, cobalt, nickel, ruthenium, rhodium, palladium, osmium, iridium, platinum, and meitnerium.

In a non-limiting embodiment, the at least one metal selected from the group consisting of Group IB metals and Group VIII metals is at least one Group IB metal.

In another non-limiting embodiment, the at least one Group IB metal is copper.

In another non-limiting embodiment, the at least one metal selected from the group consisting of Group IB metals and Group VIII metals is at least one Group VIII metal.

In another non-limiting embodiment, the at least one Group VIII metal is iron.

In yet another non-limiting embodiment, the at least one Group VIII metal is palladium.

In a non-limiting embodiment, the at least one Group IIB metal is zinc.

In a further non-limiting embodiment, the catalyst comprises a zeolite, such as, for example, mordenite, copper, and zinc.

In yet another non-limiting embodiment, the catalyst comprises a zeolite, such as, for example, mordenite, iron, and zinc.

In another non-limiting embodiment, the catalyst comprises a zeolite at least one Group IIB metal, at least one Group IB metal, and at least one Group VIII metal. In a further non-limiting embodiment, when the catalyst comprises a zeolite, at least one Group IIB metal, at least one Group IB metal, and at least one Group VIII metal, the at least one Group VIII is selected from the group consisting of palladium, platinum, and nickel.

In yet another non-limiting embodiment, the catalyst comprises a zeolite, such as, for example, mordenite, copper, zinc, and palladium.

In yet another non-limiting embodiment, the catalyst is free of halogens and halogen-containing compounds, including, but not limited to, iodine and iodine-containing compounds.

In a non-limiting embodiment, the at least one Group IB metal and/or at least one Group VIII metal, and the at least one Group IIB metal, are present in the catalyst at a molar ratio of at least one Group IB metal and/or at least one Group VIII metal to at least one Group IIB metal of from about 0.01 to about 20. In another non-limiting embodiment the at least one Group IB metal and/or at least one Group VIII metal, and the at least one Group IIB metal are present in the catalyst at a molar ratio of at least one Group IB metal and/or at least one Group VIII metal to Group IIB metal of from about 0.1 to about 5.

In general, the zeolites employed in the present invention contain alumina ($Al_2O_3$) and silica ($SiO_2$), i.e., the zeolites are aluminosilicate materials. In a non-limiting embodiment, the at least one Group IB metal and/or at least one Group VIII metal, is (are) present in the catalyst at a molar ratio of at least one Group IB metal and/or at least one Group VIII metal to aluminum of from about 0.001 to about 0.5. In another non-limiting embodiment, the at least one Group IB metal and/or at least one Group VIII metal is (are) present in the catalyst at a molar ratio of Group IB metal and/or at least one Group VIII metal to aluminum of from about 0.1 to about 0.5.

In a non-limiting embodiment, the at least one Group IIB metal is present in the catalyst at a molar ratio of Group IIB metal to aluminum of from about 0.001 to about 0.5. In another non-limiting embodiment, the at least one Group IIB metal is present in the catalyst at a molar ratio of Group IIB metal to aluminum of from about 0.1 to about 0.5.

The catalysts of the present invention, in a non-limiting embodiment, may be prepared by adding the at least one Group IB metal, such as copper, for example, and/or the at least one Group VIII metal, such as iron, for example, and the at least one Group IIB metal, such as zinc, for example, to the zeolite, such as a mordenite zeolite, for example, through a liquid-based ion-exchange process.

In another non-limiting embodiment, the catalyst is prepared by adding a powder precursor of at least one Group IB metal, such as copper, for example, and/or at least one Group VIII metal, such as iron, for example, and a powder precursor of the at least one Group IIB metal, such as zinc, for example, to the dried zeolite, such as a mordenite zeolite, for example, through a solid state ion-exchange process.

In yet another non-limiting embodiment, the catalyst is prepared by adding a precursor, such as a powder or liquid precursor, of at least one Group IB metal, such as copper, for example, and/or at least one Group VIII metal, such as iron, for example, and a powder precursor of the at least one Group IIB metal, such as zinc, for example, to the dried zeolite, such as a mordenite zeolite, for example, through an incipient wetness or a dry impregnation procedure.

When the catalyst further comprises palladium, the palladium may be added either by a liquid-based ion exchange process, a solid-state ion exchange process, or by a dry impregnation technique. In a non-limiting embodiment, the at least one Group IB metal and/or the at least one Group VIII metal, and the at least one Group IIB metal are added to the zeolite by a liquid-based ion exchange process followed by adding the palladium to the zeolite by a dry impregnation technique.

In another non-limiting embodiment, the catalyst is prepared by synthesizing nanoparticles containing the at least one Group IB metal, such as copper, for example, and/or at least one Group VIII metal, such as iron, for example, and the at least one Group IIB metal, such as zinc, for example, and palladium, in the presence of a stabilizer and depositing these nanoparticles onto the zeolite, such as a mordenite zeolite.

Thus, there is prepared a catalyst which comprises a zeolite that is impregnated with at least one Group IB metal and/or at least one Group VIII metal, and at least one Group IIB metal, and, in some cases, also may be impregnated with palladium as well. Such a catalyst then may be used to catalyze the reactions of dimethyl ether to produce methyl acetate by carbonylation.

In a non-limiting embodiment, the catalyst is pretreated prior to reaction. In a non-limiting embodiment, the catalyst is calcined in a high temperature treatment. In order to avoid damage to the zeolite, such as by steaming for example, the catalyst is heated stepwise. In a non-limiting embodiment, the initial calcination step is carried out using a gas comprising oxygen and an inert gas. The catalyst then could be used immediately for reaction following this calcination step or could be reduced further by utilizing a reducing agent.

Applicants have discovered that, if the catalyst based on the sodium form of a zeolite, such as mordenite, is contacted with a gas comprising oxygen and an inert gas, followed by contacting the catalyst with a gas comprising hydrogen and an inert gas, one achieves improved conversion of the dimethyl ether to methyl acetate. Thus, in accordance with an aspect of the present invention, there is provided a method of treating a catalyst comprising a sodium form of a zeolite, at least one group IB metal and/or at least one Group VIII metal, and at least one Group IIB metal. The method comprises contacting the catalyst with a first gas comprising oxygen and an inert gas. The catalyst then is contacted with a second gas comprising hydrogen and an inert gas.

The zeolite may be selected from the zeolites hereinabove described, and, in a non-limiting embodiment, the zeolite is a mordenite zeolite.

In a non-limiting embodiment, the at least one Group IB metal is copper. In another non-limiting embodiment, the at least one Group VIII metal is iron. In another non-limiting embodiment, the at least one Group MB metal is zinc. In yet another non-limiting embodiment, the catalyst further comprises palladium, and/or another platinum group metal.

In a non-limiting embodiment, the palladium and/or other platinum group metals, if present, is (are) present in an amount of from about 0.01 mole % to about 25 mole % relative to the aluminum content in the zeolite. In another non-limiting embodiment, the palladium and/or other platinum group metals, if present, is (are) present in an amount of from about 1 mole % to about 10 mole % relative to the aluminum content in the zeolite. In yet another non-limiting embodiment, the palladium and/or other platinum group metals, if present, is (are) present in an amount of from about 3 mole % relative to the aluminum content in the zeolite.

In another non-limiting embodiment, the catalyst is free of halogens and halogen-containing compounds, including, but not limited to, iodine and iodine-containing compounds. In yet another non-limiting embodiment, the reaction feed also is free of halogens and halogen-containing compounds.

In a non-limiting embodiment, the at least one Group IB metal and/or at least one Group VIII metal, and the at least one Group IIB metal may be present in the molar ratios of Group IB metal and/or Group VIII metal, to Group IIB metal hereinabove described.

In another non-limiting embodiment, the at least one Group IB metal and/or at least one Group VIII metal is (are) present in the catalyst at molar ratios of the at least one Group IB metal and/or at least one Group VIII metal, to aluminum as hereinabove described.

In yet another non-limiting embodiment, the at least one Group IIB metal is present in the catalyst at molar ratios of the at least one Group IIB metal to aluminum as hereinabove described.

In a non-limiting embodiment, the inert gas in the first gas is helium.

In another non-limiting embodiment, the inert gas in the first gas is nitrogen.

In a non-limiting embodiment, when the catalyst is contacted with the first gas, the catalyst is heated by the first gas to a temperature of from about 20° C. to about 800° C. In another non-limiting embodiment, the catalyst is heated by the first gas to a temperature of from about 20° C. to about 550° C.

In a non-limiting embodiment, oxygen is present in the first gas in an amount of from about 1 vol. % to about 20 vol. %. In another non-limiting embodiment, oxygen is present in the first gas in an amount of from about 5 vol. % to about 15 vol. %. In yet another non-limiting embodiment, oxygen is present in the first gas in an amount of about 10 vol. %.

In a non-limiting embodiment, the inert gas, such as helium or nitrogen, is present in the first gas in an amount of from about 80 vol. % to about 99 vol. %. In another non-limiting embodiment, the inert gas, such as helium or nitrogen, is present in the first gas in an amount of from about 85 vol. % to about 95 vol. %. In yet another non-limiting embodiment, the inert gas, such as helium or nitrogen, is present in the first gas in an amount of about 90 vol. %.

In a non-limiting embodiment, the inert gas in the second gas is argon or nitrogen.

In a non-limiting embodiment, the catalyst is heated by the second gas to a temperature of from about 300° C. to about 800° C. In another non-limiting embodiment, the catalyst is heated by the second gas to a temperature of from about 325° C. to about 650° C.

In a non-limiting embodiment, hydrogen is present in the second gas in an amount of from about 1 vol. % to about 100 vol. %. In another non-limiting embodiment, hydrogen is present in the second gas in an amount of from about 9 vol. % to about 11 vol. %. In yet another non-limiting embodiment, hydrogen is present in the second gas in an amount of about 10 vol. %.

In a non-limiting embodiment, the inert gas, such as argon or nitrogen, is present in the second gas in an amount of up to about 99 vol. %. In another non-limiting embodiment, the inert gas, such as argon or nitrogen, is present in the second gas in an amount of from about 89 vol. % to about 91 vol. %. In yet another non-limiting embodiment, inert gas, such as argon or nitrogen, is present in the second gas in an amount of about 90 vol. %.

Also, Applicants have discovered that, if the catalyst based on the ammonium or acidic form of a zeolite, such as mordenite, is contacted only with a gas comprising oxygen and an inert gas, one achieves improved conversion of the dimethyl ether to methyl acetate as compared to contacting the zeolite first with a gas comprising oxygen and an inert gas followed by contacting the zeolite with a second gas comprising hydrogen and an inert gas. Thus, in accordance with an aspect of the present invention there is provided a method of treating a catalyst comprising: (i) an ammonium or acidic or protonated form of the zeolite; (ii) at least one Group IIB metal; and (iii) at least one metal selected from the group consisting of Group IB metals and Group VIII metals. The method consists essentially of contacting the catalyst with a gas comprising oxygen and an inert gas.

The zeolite, in a non-limiting embodiment, is selected from those hereinabove described. In another non-limiting embodiment, the zeolite is a mordenite zeolite.

In a non-limiting embodiment, the zeolite, Group IB metal and/or Group VIII metal, and Group IIB metal may be those hereinabove described. In another non-limiting embodiment, the catalyst further comprises palladium, and/or another platinum group metal.

In a non-limiting embodiment, the palladium and/or other platinum group metal, if present, is (are) present in the amounts hereinabove described.

In another non-limiting embodiment, the catalyst is free of halogens and halogen-containing compounds, including, but not limited to, iodine and iodine-containing compounds. In yet another non-limiting embodiment, the reaction feed also is free of halogen and halogen-containing compounds.

In non-limiting embodiments, the at least one Group IB metal and/or at least one Group VIII metal, and the at least one Group IIB metal are present in the molar ratios of at least one Group IB metal and/or at least one Group VIII metal, to Group IIB metal hereinabove described, the at least one Group IB metal and/or at least one Group VIII metal is (are) present in the catalyst at molar ratios of the at least one Group IB metal and/or at least one Group VIII metal, to aluminum as hereinabove described, and the at least one Group IIB metal is present in the catalyst at molar ratios of the at least one Group IIB metal to aluminum as hereinabove described.

In a non-limiting embodiment, the inert gas is helium. In another non-limiting embodiment, the inert gas is nitrogen.

In a non-limiting embodiment, when the catalyst is contacted with the gas, the catalyst is heated by the gas to a temperature of from about 20° C. to about 800° C. In another non-limiting embodiment, the catalyst is heated by the gas to a temperature of from about 20° C. to about 550° C.

In a non-limiting embodiment, oxygen is present in the gas in an amount of from about 1 vol. % to about 20 vol. %. In another non-limiting embodiment, oxygen is present in the gas in an amount of from about 5 vol. % to about 15 vol. %. In yet another non-limiting embodiment, oxygen is present in the gas in an amount of about 10 vol. %.

In a non-limiting embodiment, the inert gas, such as helium or nitrogen, is present in the gas in an amount of from about 80 vol. % to about 99 vol. %. In another non-limiting embodiment, the inert gas, such as helium or nitrogen, is present in the gas in an amount of from about 85 vol. % to about 95 vol. %. In yet another non-limiting embodiment, the inert gas, such as helium or nitrogen, is present in the gas in an amount of about 90 vol. %.

The aforementioned metal-loaded zeolites are used to catalyze the reaction of dimethyl ether with carbon monoxide to produce methyl acetate. In a non-limiting embodiment, the inlet reactant gas contains dimethyl ether and carbon monoxide. The carbon monoxide may be present in stoichiometric excess. In addition to the dimethyl ether and carbon monoxide, the feed also may contain some hydrogen and inert gas. Using the aforementioned metal-loaded zeolite catalysts, the main byproduct of reaction appears to be methanol.

In a non-limiting embodiment, the molar ratio of carbon monoxide to dimethyl ether is from about 1:1 to about 100:1. In another non-limiting embodiment, the molar ratio of carbon monoxide to dimethyl ether is from about 5:1 to about 50:1. In yet another non-limiting embodiment, the ratio of carbon monoxide to dimethyl ether is from about 21.2:1 to about 46.5:1.

In a non-limiting embodiment, the molar quantity of carbon monoxide present in the inlet reactant gas is from about 10 mol % to about 95 mol %. In another non-limiting embodiment, the molar quantity of carbon monoxide present in the inlet reactant gas is from about 50 mol % to about 95 mol %. In yet another non-limiting embodiment, the molar quantity of carbon monoxide in the inlet reactant gas is from about 50.8 mol % to about 93 mol %.

In a non-limiting embodiment, the molar quantity of dimethyl ether present in the inlet reactant gas is from about 1 mol % to about 49 mol % insofar as the molar amount of dimethyl ether does not exceed the molar amount of carbon monoxide in the inlet reactant gas. In another non-limiting embodiment, the molar quantity of dimethyl ether present in the inlet reactant gas is from about 2 mol % to about 20 mol %. In yet another non-limiting embodiment, the molar quantity of dimethyl ether present in the inlet reactant gas is from about 2.0 mol % to about 2.4 mol %.

There also may be present some hydrogen in the inlet reactant gas. This hydrogen may be largely an uncontrolled quantity or may be added so as to enhance the stability and selectivity of the catalyst. In a non-limiting embodiment, the molar quantity of hydrogen in the inlet reactant gas is from about 0.1 mol % to about 20 mol %. In another non-limiting embodiment, the molar quantity of hydrogen in the inlet reactant gas is from about 2 mol % to about 10 mol %. In yet another non-limiting embodiment, the molar quantity of hydrogen in the inlet reactant gas is from about 2.86 mol % to about 3.11 mol %.

There also may be present some amount of inert gas in the inlet reactant gas. This can be either helium, argon, or nitrogen. The purpose of the inert gas is to facilitate effective management of heat generated by the reaction as well as to serve as a standard for analysis instruments. In yet another non-limiting embodiment, the inert gas used is helium.

In a non-limiting embodiment, the molar quantity of inert gas present in the inlet reactant gas is up to about 50 mol %. In another non-limiting embodiment, the molar quantity of inert gas present in the inlet reactant gas is from about 3 mol % to about 45 mol %. In yet another non-limiting embodiment, the molar quantity of inert gas present in the inlet reactant gas is from about 5 mol % to about 43.69 mol %.

In another non-limiting embodiment, all or a portion of the inert gas may be replaced by gas and/or vapor that is recycled as some or all of the reaction product stream. This can be a fraction of the product stream or selected components of the product stream with condensable and other components removed, for example. The recycled gas and/or vapor may manage the heat generated by the reaction and act as a heat transfer medium.

In a non-limiting embodiment, the temperature of the catalyst bed during the reaction is maintained between about 180° C. and about 300° C. In another non-limiting embodiment, the temperature of the catalyst bed during the reaction is maintained between about 200° C. and about 250° C. In yet another non-limiting embodiment, the temperature of the catalyst bed is maintained between about 210° C. and 220° C.

In a non-limiting embodiment, the reactor is maintained at a total pressure between about 1 bar and about 100 bar. In another non-limiting embodiment, the reactor is maintained at a total pressure between about 10 bar and about 50 bar. In yet another non-limiting embodiment, the reactor is maintained at a total pressure of from about 10 bar to about 20 bar.

In a non-limiting embodiment, the carbonylation reaction may be carried out at an inert-exclusive weight hourly space velocity (WHSV, STP) between about 0.01 $h^{-1}$ and about 100 $h^{-1}$. In another non-limiting embodiment, the carbonylation reaction may be carried out at an inert-exclusive WHSV (STP) of between about 0.1 $h^{-1}$ and about 20 $h^{-1}$. In yet another non-limiting embodiment, the carbonylation reaction is carried out at an inert-exclusive WHSV (STP) of between about 1 $h^{-1}$ and about 10 $h^{-1}$.

In a non-limiting embodiment, the carbonylation reaction is effected at a gas hourly space velocity (GHSV) of from about 500 to about 10,000 $h^{-1}$. In another non-limiting embodiment, the carbonylation reaction is effected at a GHSV of from about 1,000 to about 7,000 $h^{-1}$. In another non-limiting embodiment, the carbonylation reaction is effected at a GHSV of from about 3,000 to about 5,000 $h^{-1}$

BRIEF DESCRIPTION OF THE DRAWINGS

The invention now will be described with respect to the drawings, wherein.

EXAMPLES

Figure 1:
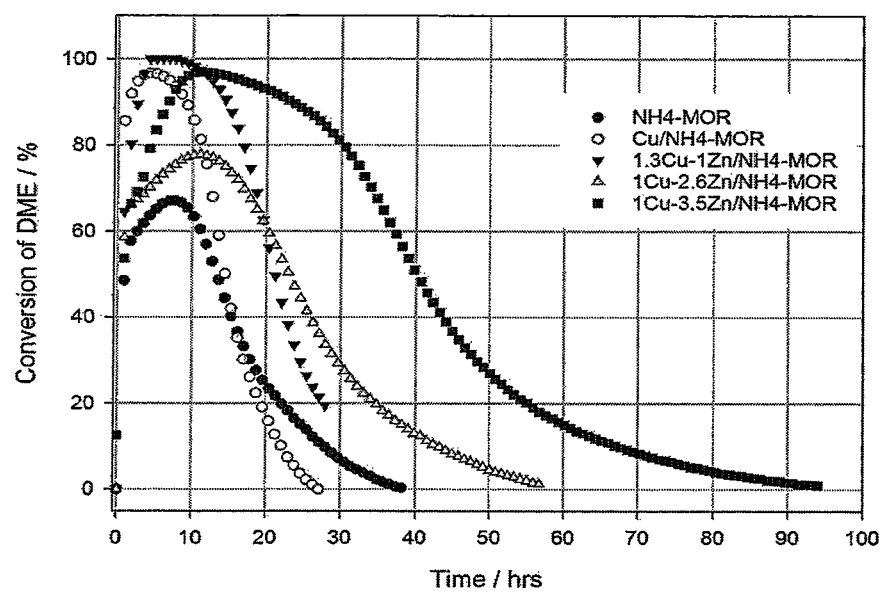
FIG. 1 is a graph showing the conversion of dimethyl ether over time on stream in the presence of $NH_4$-MOR (Example 1), Cu/$NH_4$-MOR (Example 2), 1.3Cu-1Zn/$NH_4$-MOR (Example 3), 1Cu-2.6Zn/$NR_4$-MOR (Example 4), and 1Cu-3.5Zn/$NH_4$-MOR catalysts (Example 5). 50.8% CO/2.4% DME/3.11% $H_2$/43.69% He, 15 ml/min (STP), 0.3 g catalyst, 20 bar, 210° C., inert-exclusive WHSV (STP) 2.1 $h^{-1}$.

The invention now will be described with respect to the following examples; it is to be understood, however, that the scope of the present invention is not intended to be limited thereby.

In the following examples, three different iterations of mordenite are used. The sodium-exchanged form (Na-MOR) was converted to the NH$_4$-MOR form via liquid-based ion-exchange using ammonium nitrate, as described in Example 1. The NH$_4$-MOR form was converted to the H-MOR form in situ, as described in Example 1.

The carbonylation reaction was carried out using a Micromeritics Autochem 2950 HP. The catalyst was loaded into a stainless steel tube with an inner diameter of 7.5 mm and a wall thickness of approximately 1 mm. Quartz wool was loaded into the stainless steel tube before and after the sample. This tube was mounted into the Autochem 2950 HP with the thermocouple positioned so that it was touching the outside of the stainless steel sample tube. The internal valves of the Autochem 2950 HP were kept at a constant temperature of 110° C. except for the sampling valve which is kept at a constant temperature of 150° C.

Pretreatment of the catalyst was conducted in the same stainless steel tube prior to a reaction. Pretreatment was conducted at slightly above atmospheric pressure. Typical pretreatment consisted of a high temperature calcination using a gas containing oxygen. This calcination may be followed by no further treatments prior to reaction. Further treatments include/but were not limited to high temperature treatment in pure inert gas or reduction in a hydrogen-containing gas at high temperature. After pretreatment, the catalyst was stored under inert gas until used in the reaction.

The Autochem 2950 HP was attached to a Pfeiffer Vacuum Thermostar GSD 320 T1 mass spectrometer. The capillary tube was maintained at a temperature of 200° C. and inlet maintained at a temperature of 120° C.

Prior to each reaction, the mass spectrometer was calibrated using the reactant mixture for carbon monoxide, dimethyl ether, helium, and hydrogen with helium being used as the internal standard for calibration and amounts based on what is reported for the cylinder by Praxair. The mass points used for determination of the concentration of relevant species were 2 amu for H$_2$. 4 amu for He, 12 amu for CO, 32 amu for MeOH, 46 amu for DME, and 74 amu for MeOAc.

When running a reaction, the stainless steel tube was heated to the reaction temperature and allowed to stabilize for approximately 30 minutes. After recalibration of the Thermostar GSD 320, the reactant gas is directed to flow through the stainless steel tube containing the catalyst and the system is pressurized to the desired reaction pressure. A general mass spectrum stair scan was started using the Thermostar GSD 320 set to measure the raw ion current for 0 to 74 amu. The raw ion current data then was converted to concentrations and molar flow rates using the calibration constants given by the Thermostar GSD 320 software.

The conversion of dimethyl ether as depicted in the figures was calculated as the fraction of the total dimethyl ether (DME) that is reacted, or:

$$X_{DME} = \frac{\text{Molar flow of } DME \text{ in inlet gas} - \text{Molar flow of } DME \text{ in effluent}}{\text{Molar Flow of } DME \text{ in inlet gas}}$$

Selectivity towards the desired products methyl acetate (MeOAc) and methanol (MeOH) was calculated based on their molar flow rates in the effluent gas and the total molar amount of dimethyl ether which was converted:

$$S_{MeOAc} = \frac{\text{Molar flow of MeOAc in effluent}}{\text{Molar flow of } DME \text{ in inlet gas} - \text{Molar flow of } DME \text{ in effluent}}$$

$$S_{MeOH} = \frac{\text{Molar flow of MeOH in effluent}}{2 \times (\text{Molar flow of } DME \text{ in inlet gas} - \text{Molar flow of } DME \text{ in effluent})}$$

In order to account for dimethyl ether not converted to methyl acetate or methanol, selectivity to others was calculated assuming 1:1 molar stoichiometry of DME to the unidentified products. The amount of other products was calculated as the difference between the amount of dimethyl ether that has been reacted and the amounts of methyl acetate and methanol in the feed. The raw ion profiles from the mass spectrometer also were considered when determining the selectivity to others. The selectivity towards other compounds is calculated as:

$$S_{others} = \frac{\begin{array}{c}\text{Molar flow of } DME \text{ in inlet gas} - \\ \text{Molar flow of } DME \text{ in effluent} - \\ \text{Molar flow of MeOAc in effluent} - \\ 0.5 \times \text{Molar flow MeOH}\end{array}}{\text{Molar flow of } DME \text{ in inlet gas} - \text{Molar flow of } DME \text{ in effluent}}$$

Selectivity to others thus includes unidentified hydrocarbons, oxygenates, as well as coke left on the catalyst. Mass balance with respect to DME was closed below 5% error. At the conditions reported in the examples below, no acetic acid was produced or detected on analysis.

Example 1—Production and Testing of Metal-Free $NH_4$-MOR Catalyst

Received Na-MOR was washed and dried overnight in an oven at 60° C. before being used in the liquid-based ion-exchange process. An $NH_4$-MOR catalyst was produced by liquid phase ion exchange of Na-MOR (Zeolyst International, Si/Al ratio of 6.5) in 1M $NH_4NO_3$ solution at 70° C. for 3 hours, followed by filtration, washing with deionized water, and drying overnight in an oven at 60° C. The ion exchange procedure was repeated 4 times with fresh 1M $NH_4NO_3$ solutions. The catalyst was denoted as $NH_4$-MOR.

Figure 2:
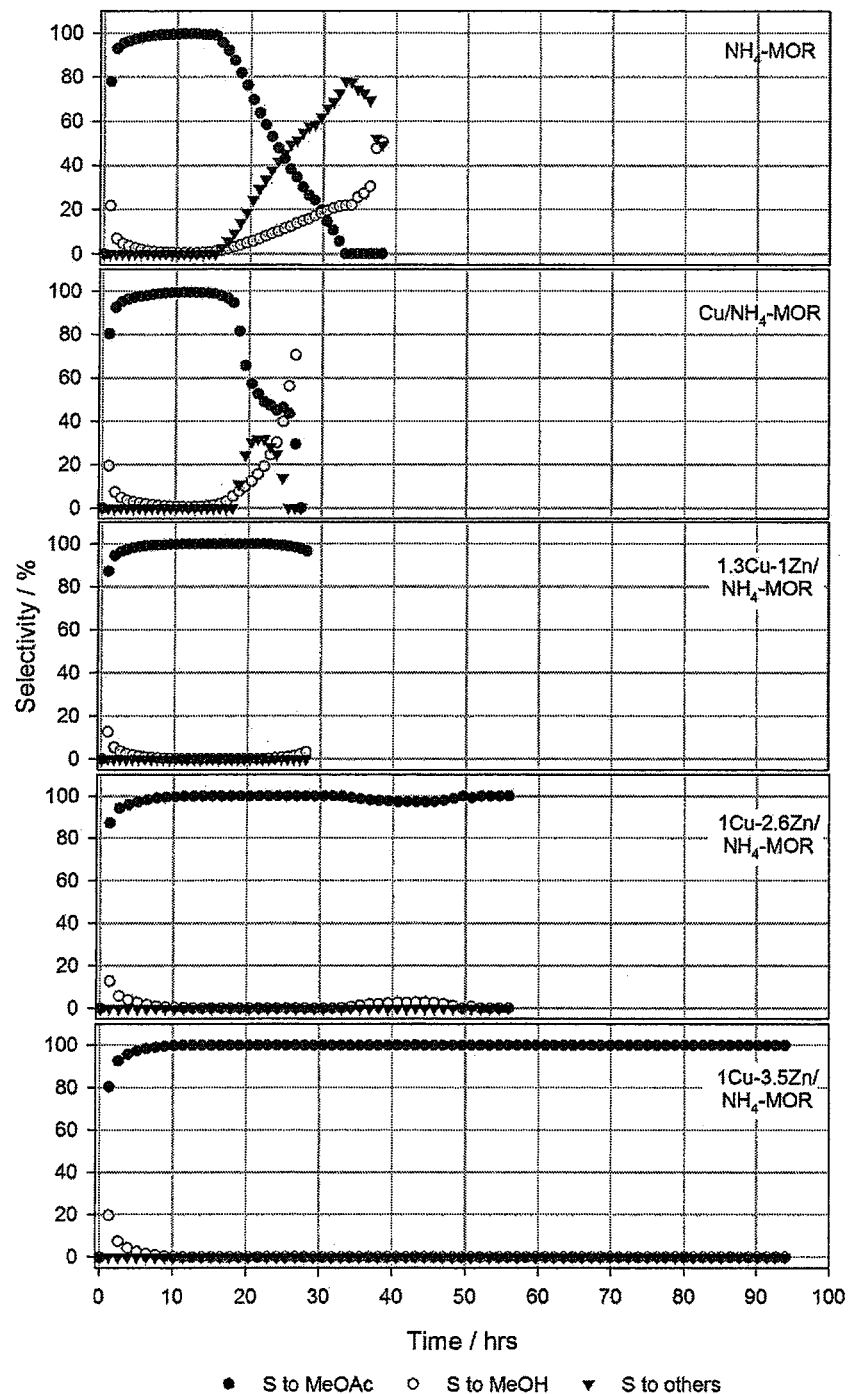
FIG. 2 is a graph showing the selectivity towards methyl acetate, methanol, and others (oxygenates and hydrocarbons) for the catalysts and reactions in FIG. 1.
Figure 3:
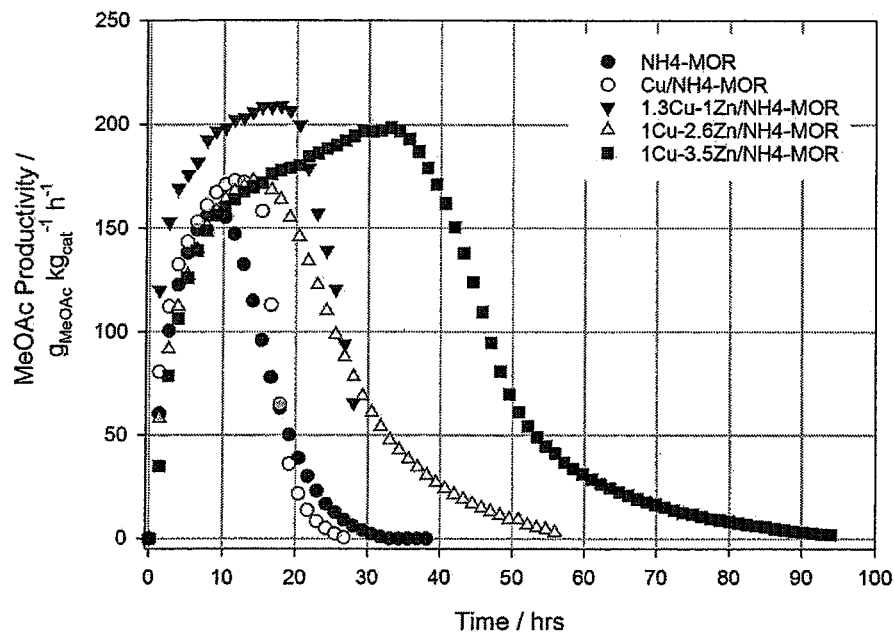
FIG. 3 is a graph showing the methyl acetate productivity for the catalysts and reactions in FIG. 1.

The catalyst was calcined in situ prior to the catalytic reaction in order to convert to H-MOR. The calcination was performed stepwise in a 10% $O_2$/90% He gas mixture to avoid sieve damage by steaming at 110° C. for 3 hours, 350° C. for 1 hour, and 550° C. for 3 hours, followed by treatment for 2 hours in He at 650° C. The catalyst then was tested in a reaction mixture of 50.8% CO/2.4% DME/3.11% $H_2$/43.69% He at 15 ml/min (STP). 0.3 g catalyst at 20 bar total pressure at 210° C. and an inert-exclusive WHSV (STP) of 2.1 $h^{-1}$. The results of the reaction are shown in FIGS. 1 through 3. The catalyst shows a short lifetime before being deactivated: as the catalyst deactivated, the formation of methanol and other oxygenates and hydrocarbons were favored equally while the selectivity towards methyl acetate decreased.

Example 2. Production and Testing of Cu/$NH_4$-MOR Catalyst

The $NH_4$-MOR material was produced as described in Example 1. It then was ion-exchanged further using 0.2 M $Cu(NO_3)_2$ aqueous solutions. The ion exchange was repeated 4 times to achieve a 2.6 wt % Cu loading, as per neutron activation analysis (NAA) of the final dried powders.

The catalyst was calcined in situ prior to the catalytic reaction to convert the $NH_4$-MOR to H-MOR. The calcination was performed step-wise in a 10% $O_2$/90% He mixture to avoid sieve damage by steaming at 110° C. for 3 hours, 350° C. for 1 hour, and 550° C. for 3 hours. The temperature then was lowered to 400° C., followed by metal reduction in 10% $H_2$/90% Ar for 20 min at 400° C. and for 1 hour at 550° C. The temperature then was lowered to 400° C., the flow was switched to He and returned to ambient temperature, followed by the catalytic test.

This catalyst was tested in a reaction mixture of 50.8% CO/2.4% DME/3.11% $H_2$/43.69% He at 15 mL/min (STP), 0.3 g of catalyst at 20 bar total pressure at 210° C., and an inert-exclusive WHSV (STP) of 2.1 $h^{-1}$. The results for the reaction are shown in FIGS. 1 through 3. The catalyst has high peak dimethyl ether conversion but deactivates quickly. The selectivity towards methyl acetate drops substantially as the catalyst deactivates with the favored product during deactivation being methanol.

Example 3—Production and Testing of 1.3Cu-1Zn/$NH_4$-MOR Catalyst

The $NH_4$-MOR catalyst was prepared as described in Example 1. This catalyst then was ion exchanged using 0.089M Cu ($NO_3$) and 0.111 M $Zn(NO_3)_2$ aqueous solutions. The ion exchange was repeated 4 times to achieve a 1.8 wt. % Cu loading and a 1.4 wt. % Zn loading, per neutron activation analysis (NAA) of the final dried powders.

The catalyst was calcined, reduced in situ, and tested in DME carbonylation as described in Example 2. The results are presented in FIGS. 1 through 3. As shown, a very high peak conversion (100%) was achieved as compared to the highest peak conversion of the H-MOR form of approximately 65%. The selectivity towards methyl acetate also was maintained at a very high level (approximately 100%) during the entirety of reaction even as the catalyst had begun to deactivate.

Example 4. Production and Testing of 1Cu-2.6Zn/$NH_4$-MOR Catalyst

The $NH_4$-MOR material was produced as described in Example 1. It was ion-exchanged further using 0.033M $Cu(NO_3)_2$ and 0.167M $Zn(NO_3)_2$ aqueous solutions; the ion-exchange was repeated 4 times to achieve a 0.9 wt % Cu loading and a 2.4 wt % Zn loading (as per NAA of the final dried powders).

The catalyst was calcined in situ prior to the catalytic reaction to convert to the H-MOR. The calcination was performed stepwise in a 10% $O_2$/90% He gas mixture to avoid sieve damage by steaming, at 110° C. for 3 hours, 350° C. for 1 hour, and 550° C. for 3 hours. The temperature then was lowered to 400° C. followed by metal reduction in 10% $H_2$/90% Ar for 20 min. at 400° C. and for 2 hours at 650° C. The temperature then was lowered to 400° C., the flow was switched to He and returned to ambient temperature, followed by the catalytic test.

The catalyst was tested in DME carbonylation as described in Example 2. The results are presented in FIGS. 1 through 3. The additional zinc has a substantial stabilizing effect on the catalyst, extending the catalyst lifetime to over 50 hours without regeneration. While some methanol is formed at the very start of reaction, the main product during the entire time of reaction is methyl acetate with a selectivity near 100%. As the catalyst deactivated, the primary product of reaction still was methyl acetate with the high selectivity of nearly 100% maintained.

Example 5 Production and Testing of 1Cu-3.5Zn/$NH_4$-MOR Catalyst

The $NH_4$-MOR material was produced as described in Example 1. It was ion-exchanged further using 0.023M $Cu(NO_3)_2$ and 0.177M $Zn(NO_3)_2$ aqueous solutions; the ion-exchange was repeated 4 times to achieve an approximate molar ratio of 1:3.5 Cu:Zn and approximate metal loading of 0.7 wt. % Cu and 2.6 wt. % Zn.

The catalyst was calcined in situ prior to the catalytic reaction to convert to the H-MOR. The calcination was performed stepwise in a 10% $O_2$/90% He gas mixture to avoid sieve damage by steaming at 110° C. for 3 hours, 350° C. for 1 hour, and 550° C. for 3 hours. The temperature then was lowered to 300° C., the flow was switched to He and returned to ambient temperature, followed by the catalytic test.

The catalyst was tested in DME carbonylation as described in Example 2. Results are presented in FIGS. 1 through 3. The additional zinc has a substantial stabilizing effect on the catalyst, extending the catalyst lifetime to over 90 hours without regeneration. While some methanol is formed at the very start of reaction, the main product during the entire time of reaction is methyl acetate with a selectivity near 100%. As the catalyst deactivated, the primary product of reaction still was methyl acetate with the high selectivity of nearly 100% maintained.

Example 6. Production and Testing of a 1Cu-2.6Zn/NH$_4$-MOR Catalyst

The 1Cu-2.6Zn/NH$_4$-MOR catalyst was prepared as described in Example 4.

The catalyst was calcined in situ, prior to the catalytic reaction to convert to the H-MOR. The calcination was performed stepwise in a 10% O$_2$/90% He gas mixture to avoid sieve damage by steaming, at 110° C. for 3 hours, 350° C. for 1 hour, and 550° C. for 3 hours. The temperature then was lowered to 400° C. followed by metal half-reduction in 10% H$_2$/90% Ar for 20 min. at 300° C. and for 2 hours at 325° C. The temperature then was lowered to 300° C., the flow was switched to He and returned to ambient temperature, followed by the catalytic test.

Figure 4:
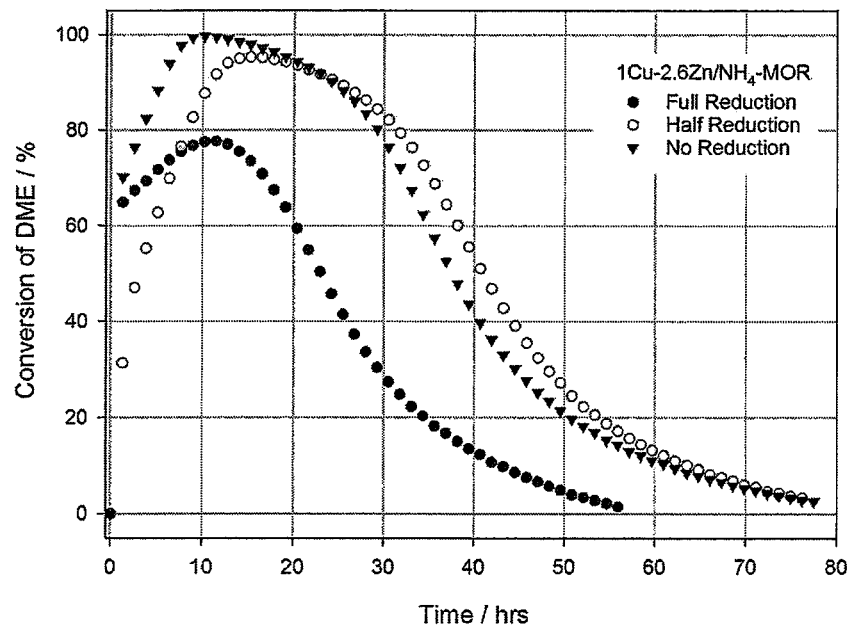
FIG. 4 is a graph showing the conversion of dimethyl ether over time on stream in the presence of 1Cu-2.6Zn/$NH_4$-MOR catalysts that were subjected to full reduction (Example 4), half reduction (Example 6), or no reduction (Example 7)
Figure 5:
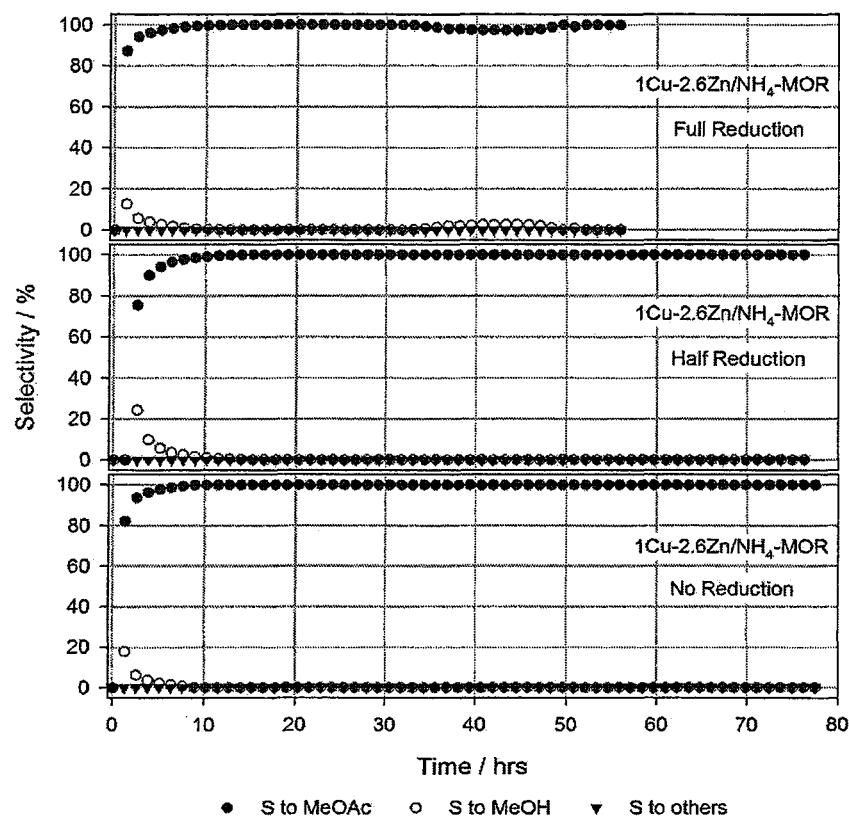
FIG. 5 is a graph showing the selectivity towards methyl acetate, methanol, and others (oxygenates and hydrocarbons) for the catalysts and reactions of Examples 4, 6 and 7.
Figure 6:
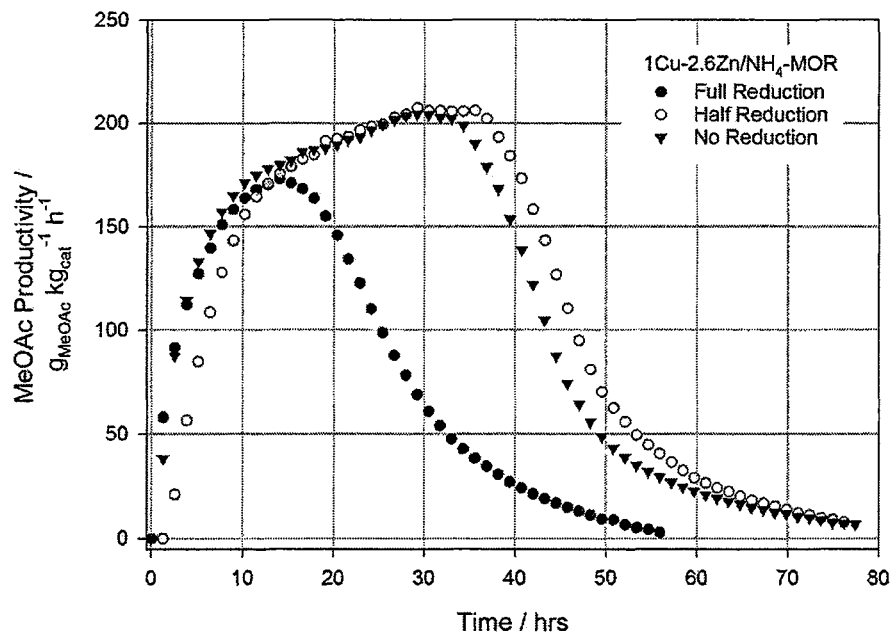
FIG. 6 is a graph showing the methyl acetate productivity for the catalysts and reactions of Examples 4, 6 and 7.

The catalyst was tested in DME carbonylation as described in Example 2. Results are presented in FIGS. 4 through 6 labelled as "half reduction". As compared to the fully reduced sample, the peak conversion of DME is substantially higher along with a greatly increased lifetime (a lifetime of 50 hours for the fully reduced 1Cu-2.6Zn/NH$_4$-MOR has been extended to 75 hours). While some methanol still is formed at the very start of reaction, the main product during the entire time of reaction is methyl acetate with a selectivity near 100%. As the catalyst deactivated, the primary product of reaction still was methyl acetate with the high selectivity of nearly 100% maintained.

Example 7. Production and Testing of a 1 Cu-2.6Zn/NH$_4$-MOR Catalyst

The 1 Cu-2.6Zn/NH$_4$-MOR catalyst was prepared as described in Example 4.

The catalyst was calcined in situ prior to the catalytic reaction to convert to the H-MOR. The calcination was performed stepwise in a 10% O$_2$/90% He gas mixture to avoid sieve damage by steaming, at 110° C. for 3 hours, 350° C. for 1 hour, and 550° C. for 3 hours. The temperature then was lowered to 300° C., the flow was switched to He and returned to ambient temperature.

The catalyst was tested in DME carbonylation as described in Example 2. Results are presented in FIGS. 4 through 6 labelled as "no reduction". As compared to the fully reduced sample, the peak conversion of DME again is substantially higher along with a greatly increased lifetime (a lifetime of 50 hours for the fully reduced 1Cu-2.6Zn/NH$_4$-MOR has been extended to 75 hours). Compared to the half-reduced 1Cu-2.6Zn/NR$_4$-MOR, peak conversion of DME is not as high but overall the same amount of MeOAc is produced. The behavior of this catalyst with no reduction was very similar to that of the half reduced sample described in Example 6. At the very start of reaction some MeOH is produced but the main product still is methyl acetate. As the catalyst deactivated, the primary product of reaction still was methyl acetate with the high selectivity of nearly 100% maintained.

Example 8. Regeneration of 1.3Cu-1Zn/NH$_4$-MOR Catalyst

The catalyst was produced and pretreated (calcined/reduced) analogously to the procedure presented in Example 3.

Figure 7:
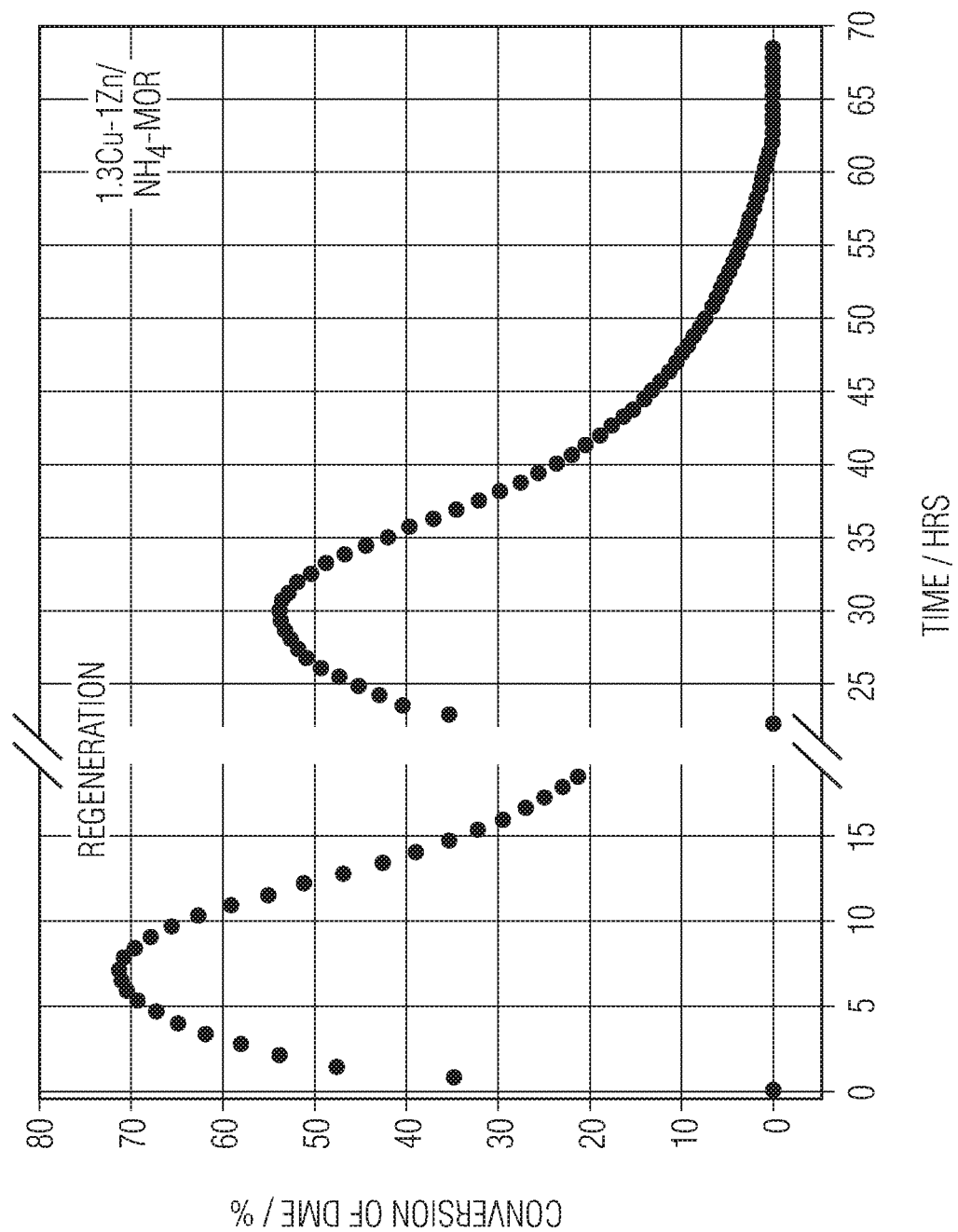
FIG. 7 is a graph showing the effect of in situ regeneration at 20 bar hydrogen on dimethyl ether conversion for a 1.3Cu-1Zn/$NH_4$-MOR catalyst (Example 8), 50.8% CO/2.4% DME/3.11% $H_2$/43.69% He, 15 mL/min (STP), 0.15 g catalyst, 20 bar, 220'C, inert-exclusive WHSV (STP) 4.1 $h^{-1}$.
Figure 8:
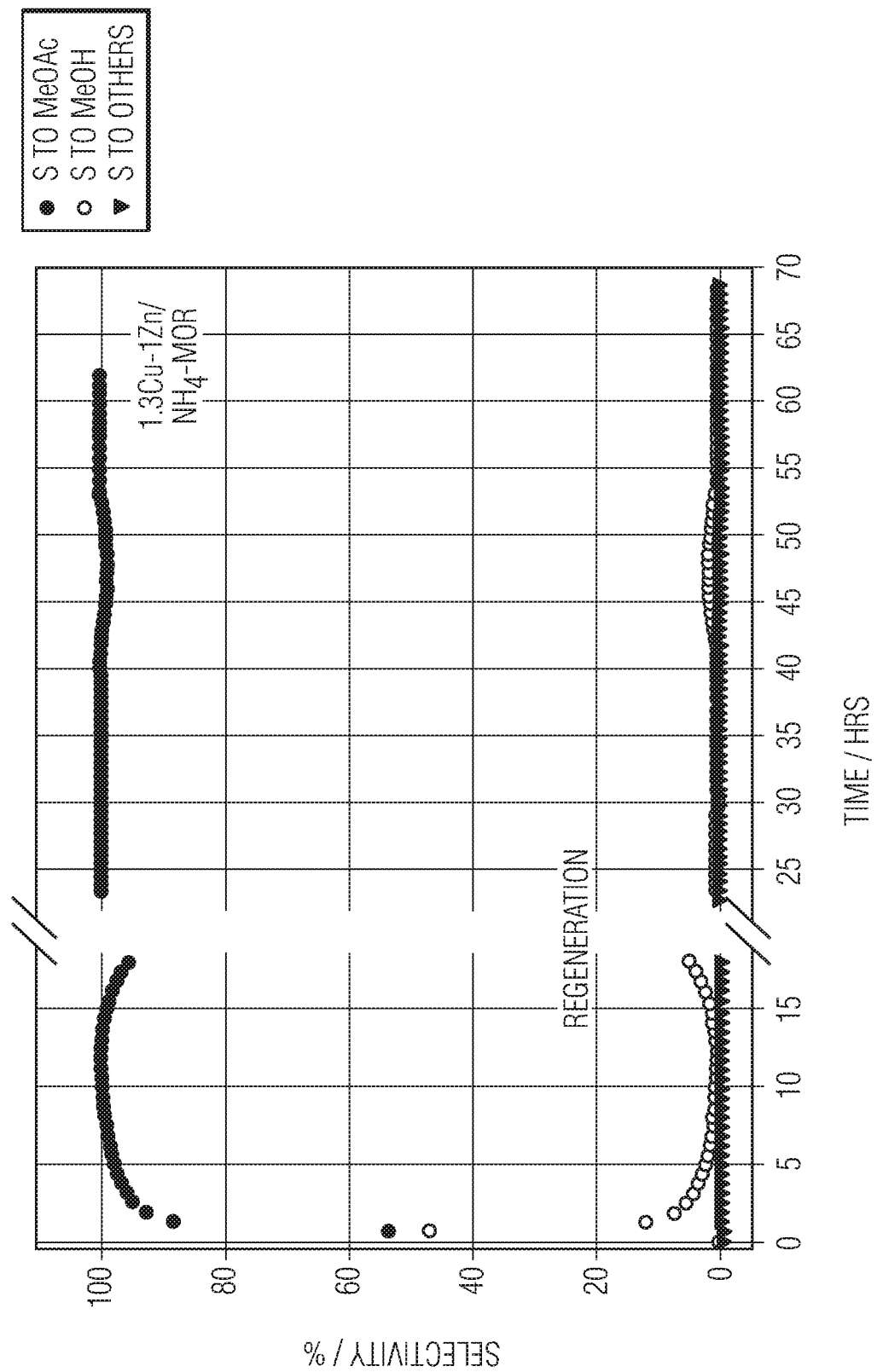
FIG. 8 is a graph showing the selectivity towards methyl acetate, methanol, and other oxygenates and hydrocarbons for the regeneration procedure in FIG. 7.
Figure 9:
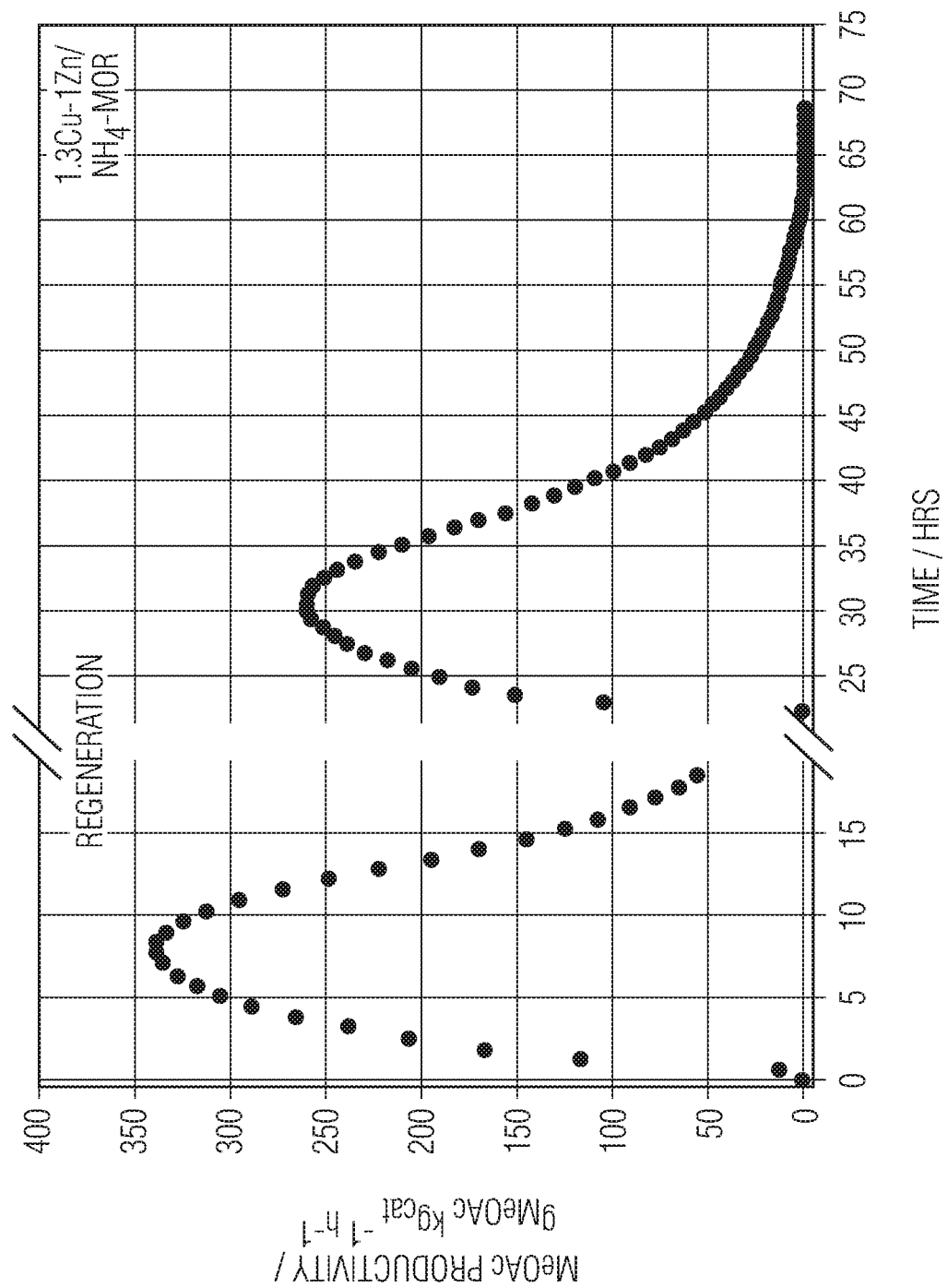
FIG. 9 is a graph showing the methyl acetate productivity for the regeneration procedure in FIG. 7.

This catalyst was tested in a reaction mixture of 50.8% CO/2.4% DME/3.11% H$_2$/43.69% He at 15 mL/min (STP), 0.15 g of catalyst at 20 bar total pressure at 220° C., and an inert-exclusive WHSV (STP) of 4.1 h$^{-1}$. After conversion of DME had dropped to about 20% and the selectivity towards MeOAc just had begun to decrease, which occurred after approximately 19 hours, the flow of 50.8% CO/2.4% DME/3.11% H$_2$/43.69% He was stopped and pure H$_2$ was introduced to the reactor. After 15 min at 220° C., the temperature was increased at a rate of 1.6° C./min to 400° C. The catalyst was kept under H$_2$ flow at 400° C. for a period of 10 hours. Hydrogen pressure was 20 bar (no regeneration could be achieved at 1 bar pressure). The reactor was depressurized and H$_2$ flow was stopped and a flow of 10% H$_2$/90% Ar was introduced. The catalyst was kept under 10% H$_2$/90% Ar flow and at 400° C. for a period of 30 min before the temperature was increased to 550° C. where it was maintained for a period of 1 h. The catalyst was cooled to 400° C. and flow through the catalyst was switched to Ar. The catalyst was cooled further to the reaction temperature of 220° C. and the reaction began again. The regenerated catalyst was tested using the same 50.8% CO/2.4% DME/3.11% H$_2$/43.69% He mixture at 15 mL/min(STP), 20 bar total pressure at 220° C., and an inert-exclusive WHSV (STP) of 4.1 h$^{-1}$. The regenerated catalyst was tested until conversion of DME dropped to 0%, which occurred at a time on stream of approximately 40 hours. The reaction results are shown in FIGS. 7 through 9. Prior to regeneration, the catalyst achieved a peak dimethyl ether conversion of approximately 72%. After regeneration, the peak conversion achieved was approximately 55%. As shown, after regeneration, the selectivity towards methyl acetate was maintained at a very high level (approximately 100%) with the only other by-product being very low levels of methanol.

Figure 10:
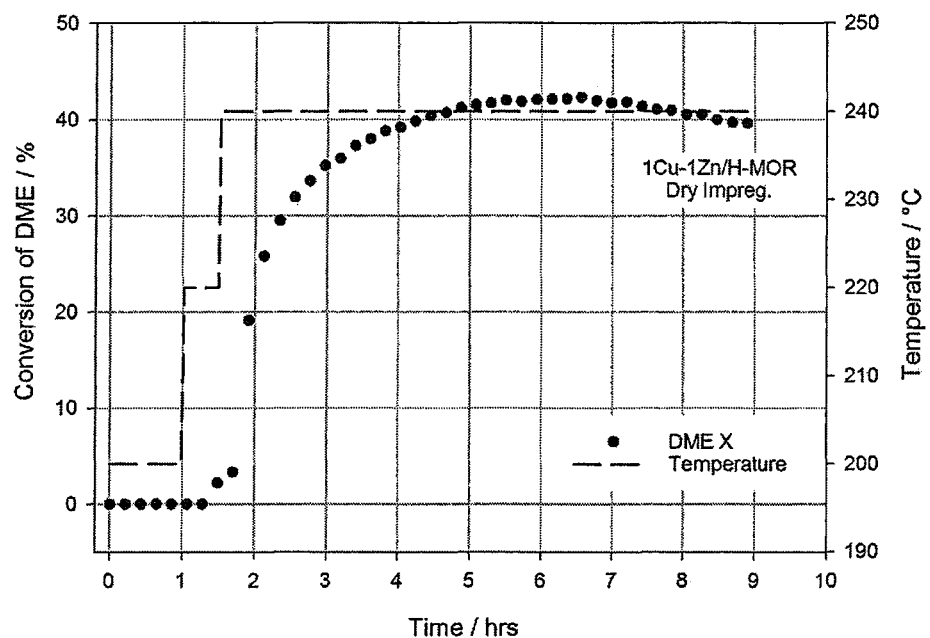
FIG. 10 is a graph showing the conversion of dimethyl ether over time on stream for the 1Cu-1Zn/HMOR catalyst synthesized via a dry impregnation method (Example 9). 93% CO/5% He/2% DME at 15 mL/min (STP), 0.3 g catalyst, 10 bar, inert-exclusive WHSV (STP) 3.6 $h^{-1}$.
Figure 11:
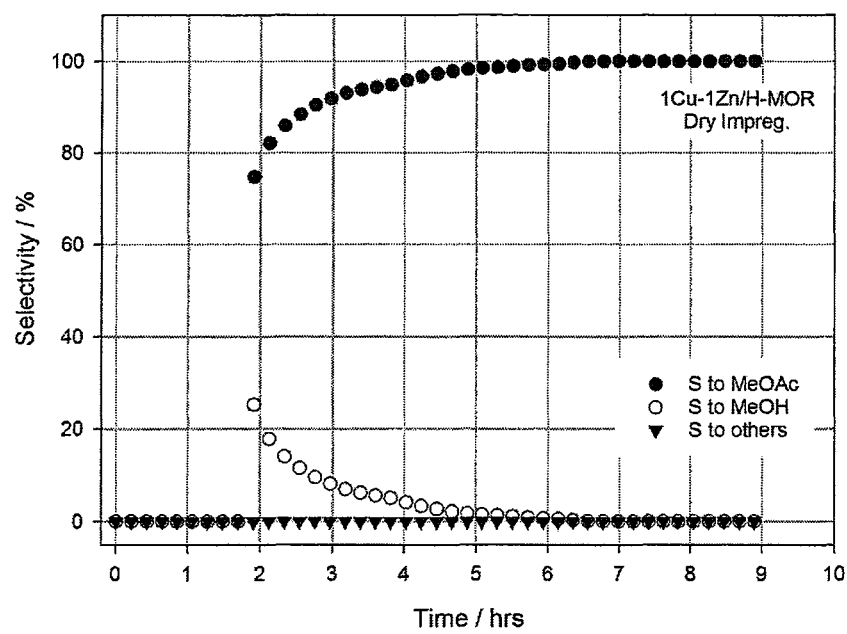
FIG. 11 is a graph showing the selectivity towards methyl acetate, methanol, and to other oxygenates and hydrocarbons for the catalyst and reaction in FIG. 10.
Figure 12:
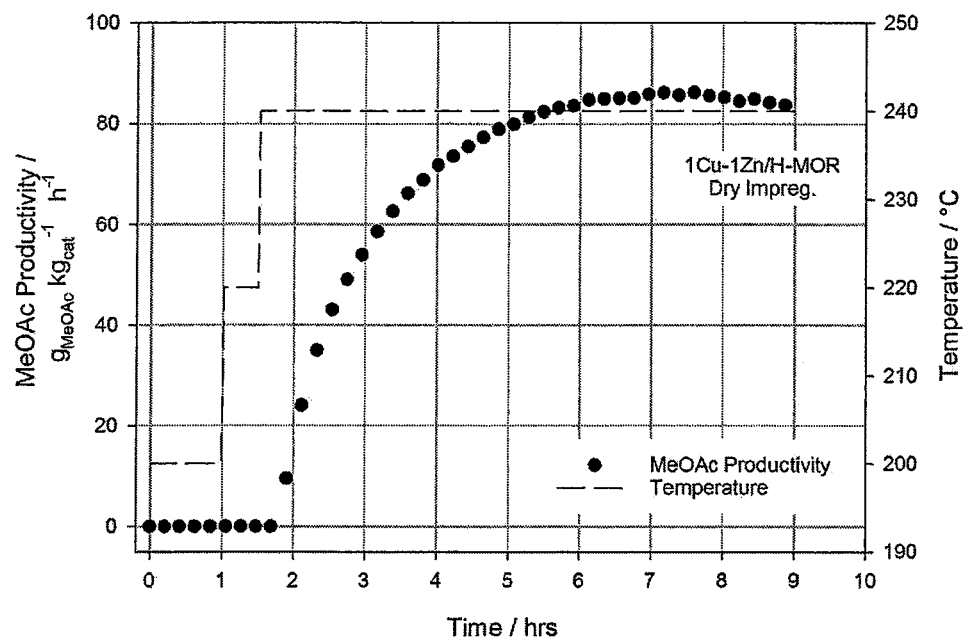
FIG. 12 is a graph showing the methyl acetate productivity over time on stream for the catalyst and reaction in FIG. 10.

Example 9. Production and Testing of 1Cu-1Zn/H-MOR Catalyst Via Dry Impregnation NH$_4$-MOR catalyst was produced as in Example 1. This NH$_4$-MOR catalyst was converted to H-MOR by heating in a furnace at 550° C. for a period of 16 hours. Cu and Zn then were loaded onto the H-MOR via a dry impregnation process. An equimolar solution of Cu(NO$_3$)$_2$ and Zn(NO$_3$)$_2$ was prepared and added dropwise while stirring and ultrasonic mixing to dry H-MOR powder until 2.5 wt % (relative to total catalyst weight) was achieved for each of Cu and Zn. The catalyst was dried overnight in an oven at 60° C. to produce 1Cu-1Zn/H-MOR. The catalyst was calcined in situ in a 10% O$_2$/90% He mixture at 550° C. followed by treatment for 2 hours in 10% H$_2$/90% Ar at 500° C. for 2 hours. The catalyst then was tested in a reaction mixture of 93% CO/5% He/2% DME at 15 mL/min (STP), 0.3 g catalyst at 10 bar total pressure starting at a temperature of 200° C., and an inert-exclusive WHSV (STP) of 3.6 h$^{-1}$. The temperature was increased during the reaction to an approximate temperature of 240° C. to facilitate higher conversion. The results of the reaction are shown in FIGS. 10 through 12. A peak DME conversion of approximately 42% was achieved with very high selectivity of nearly 100% towards methyl acetate. The example shows applicability of the dry impregnation method in the catalyst production.

Example 10. Production and Testing of Cu/Na-MOR Catalyst

The Na-MOR was ion-exchanged using a 0.2 M aqueous solution of Cu(NO$_3$)$_2$ at a volume of 50 mL/g of Na-MOR.

The slurry was stirred and kept at 70° C. for 3 hours before being vacuum filtered to retrieve the catalyst. The catalyst was dried overnight at 60° C. This ion-exchange procedure was repeated 4 times to achieve a final Cu loading of 4.6 wt %.

The catalyst was calcined in situ prior to the catalytic reaction. Calcination was performed at 550° C. in a flowing dry 10% $O_2$/90% He gas mixture for 3 hours followed by treatment in flowing 10% $H_2$/90% Ar at 500° C. for a period of 2 hours. The catalyst was stored under He and returned to ambient temperature, followed by the catalytic test.

The catalyst was tested in a reaction mixture of 50.8% CO/2.4% DME/3.11% $H_2$/43.69% He at 15 mL/min (STP), 0.3 g of catalyst at 20 bar total pressure at 230° C. and an inert-exclusive WHSV (STP) of 2.1 $h^{-1}$. The results are presented in FIGS. 13 through 15. The lifetime of the catalyst is short and selectivity towards methyl acetate begins to decrease as other products and methanol increasingly are favored.

Example 11. Production and Testing of Zn/Na-MOR Catalyst

Na-MOR was ion-exchanged using a 0.2 M aqueous solution of $Zn(NO_3)_2$. The ion exchange was repeated 4 times to achieve a 4.8 wt % Zn loading, per neutron activation analysis of the final dried powders.

The catalyst was calcined in situ prior to the catalytic reaction. Calcination was performed at 550° C. in a flowing dry 10% $O_2$/90% He gas mixture for 3 hours followed by treatment in flowing 10% $H_2$/90% Ar at 550° C. for a period of 2 hours. The catalyst was stored under He and returned to ambient temperature, followed by the catalytic test.

The catalyst was tested in a reaction mixture of 50.8% CO/2.4% DME/3.11% $H_2$/43.69% He at 15 mL/min (STP), 0.3 g of catalyst at 20 bar total pressure at a starting temperature of 230° C. and an inert-exclusive WHSV (STP) of 2.1 $h^{-1}$. The temperature was increased to 270° C. during the time on stream. This catalyst showed no activity at any of the temperatures tested, indicating that zinc alone does not facilitate the carbonylation of DME.

Example 12. Production and Testing of 1Cu-1Zn/Na-MOR Catalyst

Na-MOR then was ion-exchanged using 0.057 M $Cu(NO_3)_2$ and 0.143 M $Zn(NO_3)_2$ aqueous solutions. The ion exchange was repeated 4 times to achieve a 2.4 wt % Cu loading and a 2.3 wt % Zn loading, per neutron activation analysis of the final dried powders.

Figure 13:
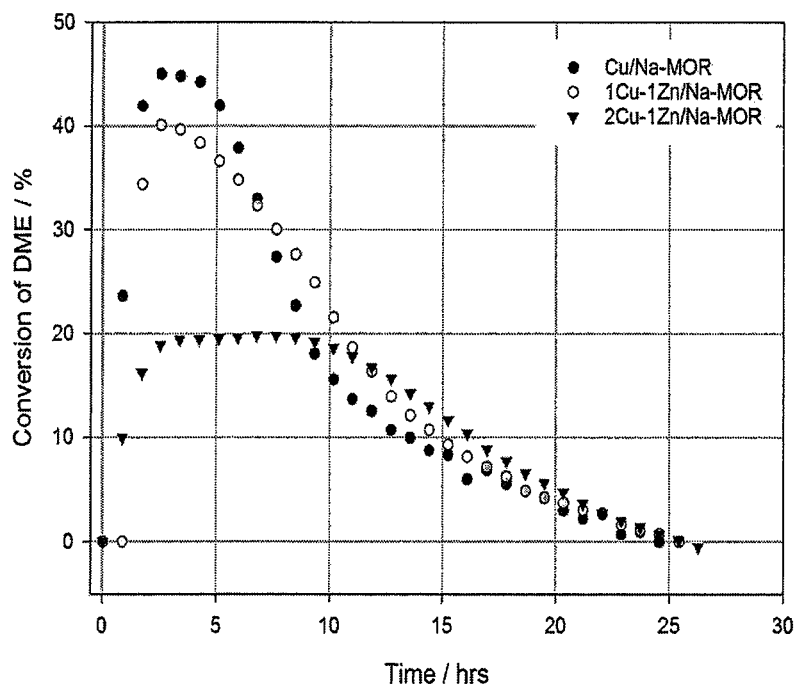
FIG. 13 is a graph showing the conversion of dimethyl ether over time on stream for Cu/Na-MOR (Example 10), 1Cu-1Zn/Na-MOR (Example 12), and 2Cu-1Zn/Na-MOR (Example 13). 50.8% CO/2.4% DME/3.11% $H_2$/43.69% He, 15 mL/min (STP), 0.3 g of catalyst, 20 bar, 230° C., inert-exclusive WHSV (STP) 2.1 $h^{-1}$.
Figure 14:
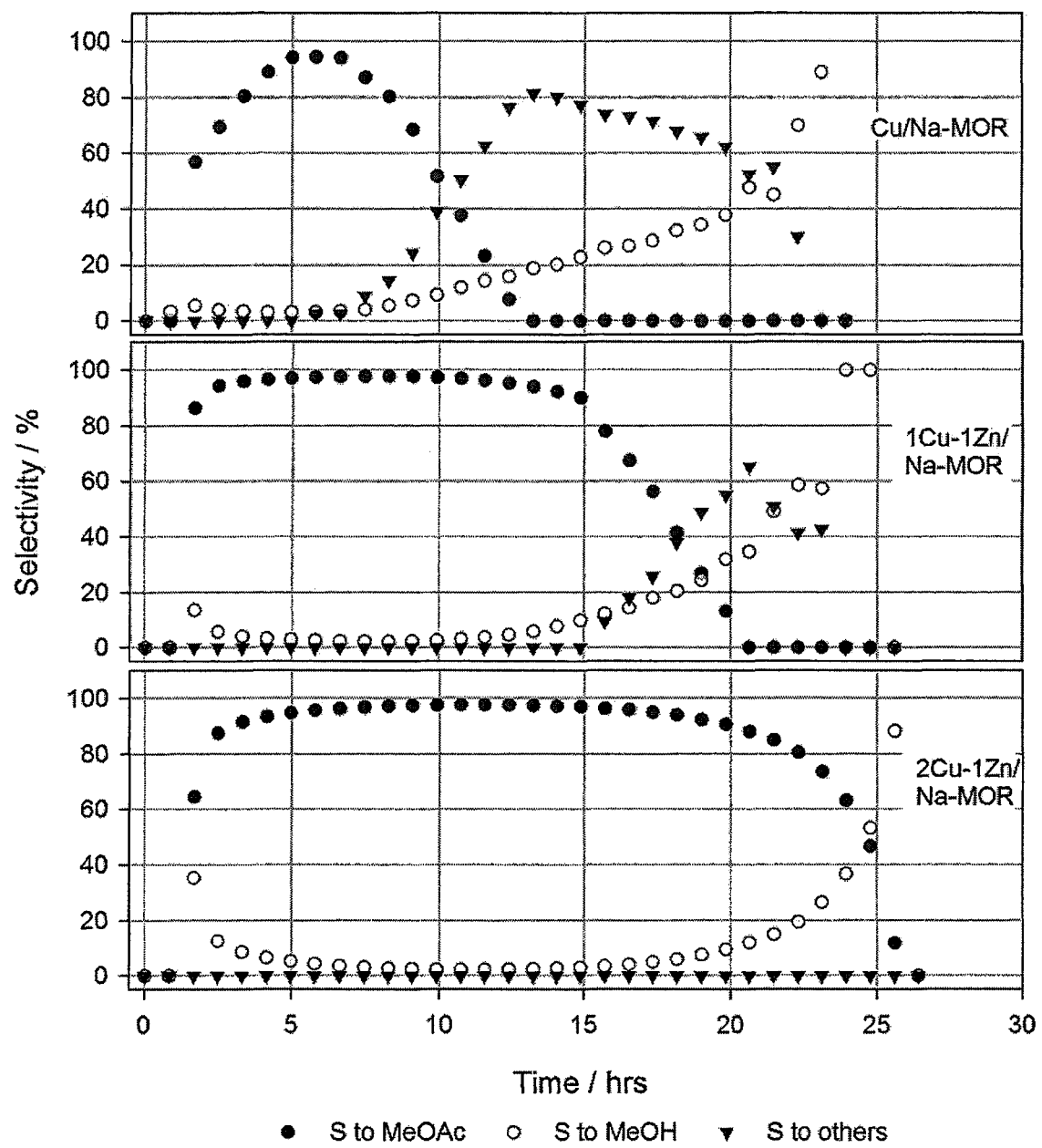
FIG. 14 is a graph showing the selectivity towards methyl acetate, methanol, and to other oxygenates and hydrocarbons over reaction time for the catalysts and reactions in FIG. 13.
Figure 15:
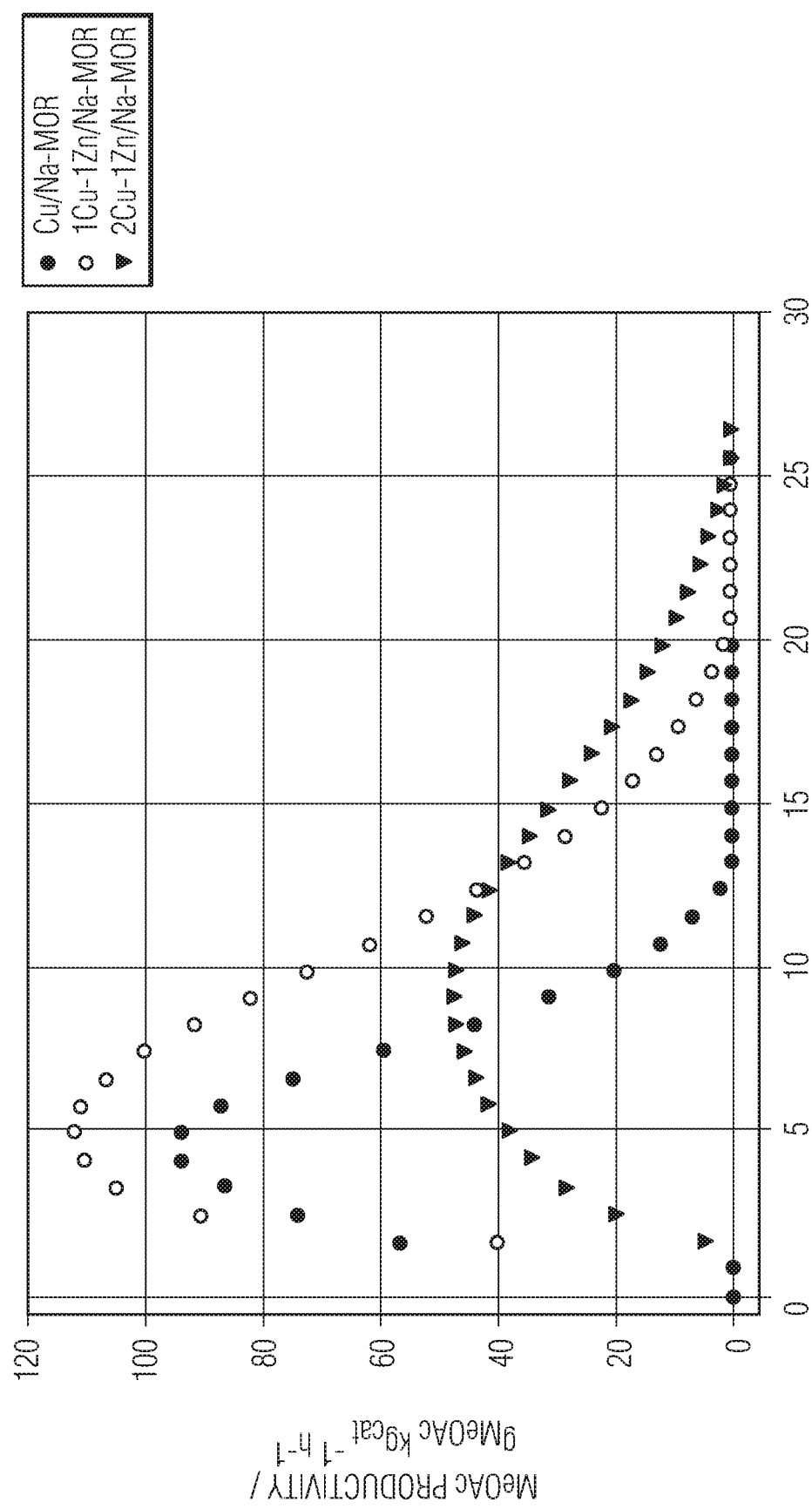
FIG. 15 is a graph showing the methyl acetate productivity for the catalysts and reactions in FIG. 13.

The catalyst was calcined, reduced, and tested in the reaction as in Example 9. The results are shown in FIGS. 13 through 15. The impact of the zinc is shown in the selectivity profiles, where the amount of other oxygenates and hydrocarbons produced during reaction is considerably lower at the end of reaction, with selectivity at the end of reaction shifting to favor methanol.

Example 13. Production and Testing of 2Cu-1Zn/Na-MOR Catalyst

Na-MOR was ion-exchanged using 0.089 M $Cu(NO_3)_2$ and 0.111 M $Zn(NO_3)_2$ aqueous solutions. The ion exchange was repeated 4 times to achieve a 3.1 wt. % Cu loading and a 1.7 wt. % Zn loading, per neutron activation analysis of the final dried powders.

The catalyst was calcined, reduced and tested in the reaction as in Example 9. The results are shown in FIGS. 13 through 15. The presence of produced oxygenates and hydrocarbon by-products is suppressed entirely with the only by-product of reaction being methanol. The addition of zinc is shown to have a positive stabilizing effect on the product profile during reaction.

Example 14. Production of 2Cu-1Zn-0.3Pd/Na-MOR Catalyst

Na-MOR was ion-exchanged using 0.089 M $Cu(NO_3)_2$ and 0.111 M $Zn(NO_3)_2$ aqueous solutions. The ion exchange was repeated 4 times to achieve a 3.1 wt. % Cu loading and a 1.7 wt. % Zn loading, per neutron activation analysis of the final dried powders.

After this procedure, a mixture of $Pd(OAc)_2$ dissolved in toluene was added dropwise to the 2Cu-1Zn/NaMOR while being stirred and sonicated. This mixture was dried overnight at 60° C. to produce a catalyst with 0.8 wt. % Pd loading as compared to total catalyst weight, forming the final 2Cu-1Zn-0.3Pd/Na-MOR catalyst.

The catalyst underwent temperature programmed reduction in situ prior to the catalytic reaction tests. Starting from ambient conditions, the catalyst was treated in 10% $H_2$/90% Ar and heated at a rate of 10° C./min to a final temperature of 750° C. before being returned to a reaction temperature of 200° C. under a low flow of He.

Figure 16:
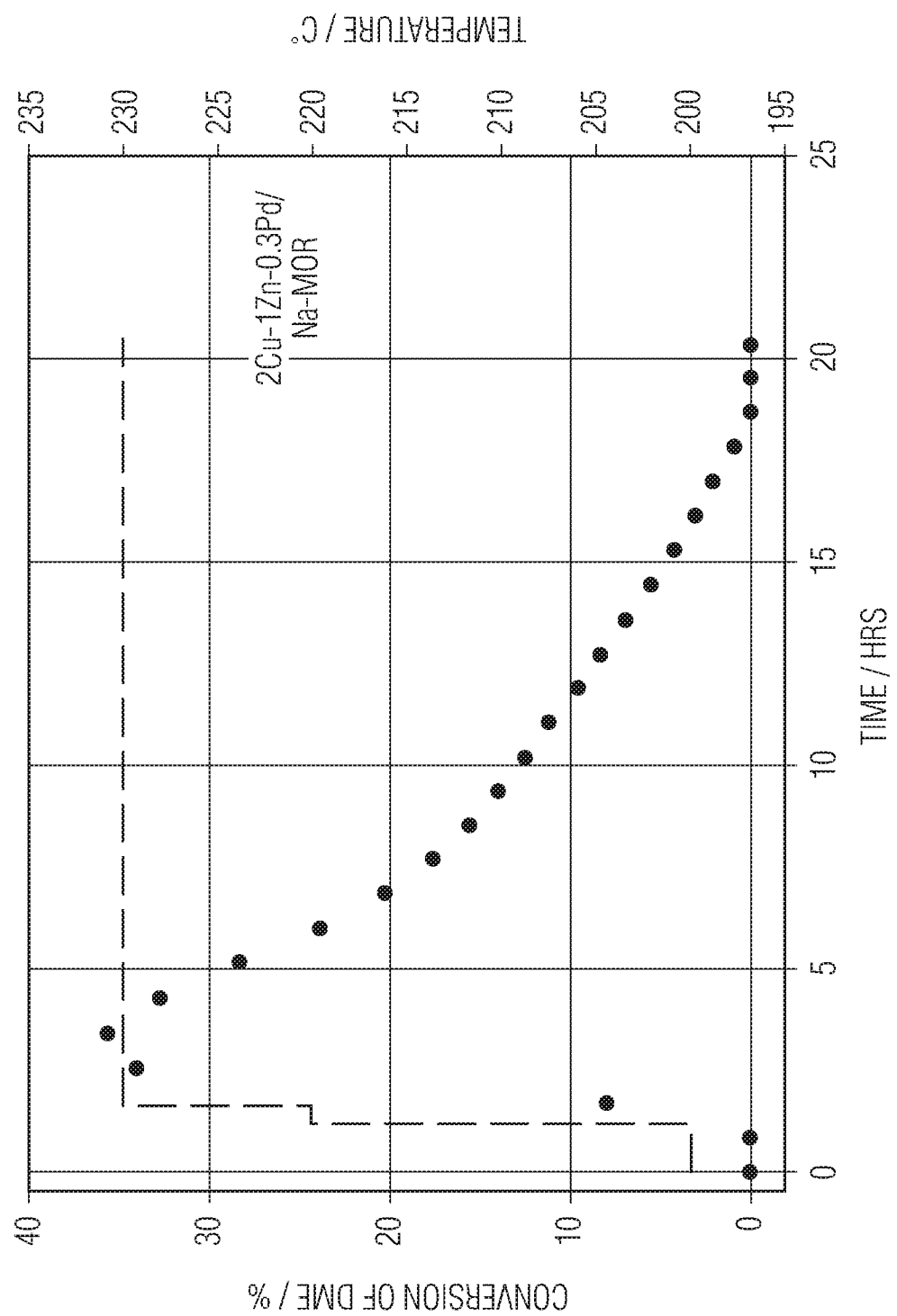
FIG. 16 is a graph showing the conversion of dimethyl ether over time on stream for a 2Cu-1Zn-0.3Pd/Na-MOR catalyst (Example 14). 93% CO/2% DME/5% He at 15 mL/min (STP), 0.3 g of catalyst, 10 bar, inert-exclusive WHSV (STP) 3.6 $h^{-1}$.
Figure 17:
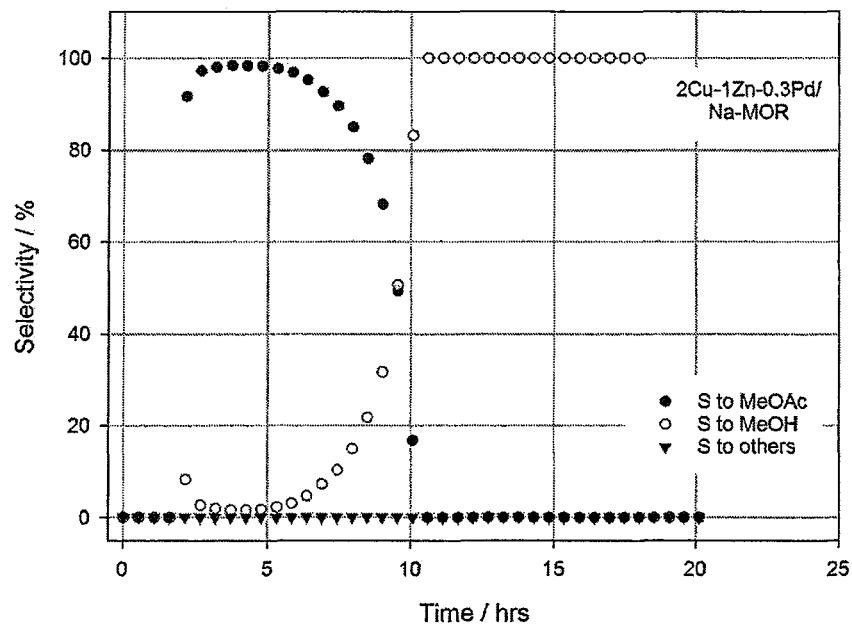
FIG. 17 is a graph showing the selectivity towards methyl acetate, methanol, and other oxygenates and hydrocarbons over time on stream for the catalyst and reaction in FIG. 16.
Figure 18:
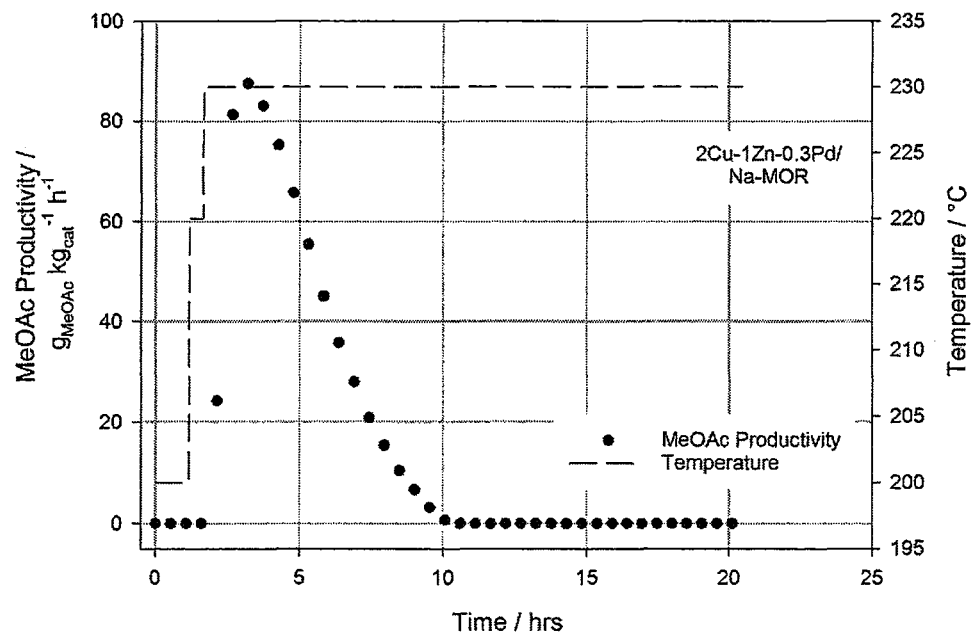
FIG. 18 is a graph showing the methyl acetate productivity for the reaction and catalyst in FIG. 16.

The catalyst was tested in a reaction mixture of 93% CO/2% DME/5% He at 15 mL/min (STP), 0.3 g of catalyst at 10 bar total pressure at a starting temperature of 200° C. and an inert-exclusive WHSV (STP) of 3.6 $h^{-1}$. Temperature was increased during time on stream to a final temperature of 230° C. The results are shown in FIGS. 16 through 18. The formation of other oxygenates and hydrocarbons was suppressed during the entirety of the reaction test.

Example 15. Production and Testing of a Cu—Zn/$Al_2O_3$ Catalyst

γ-$Al_2O_3$ (Sigma-Aldrich, 0.58 nm pore size, 150 mesh) was impregnated via an incipient wetness technique using solutions of $Cu(NO_3)_2$ and $Zn(NO_3)_2$. The powder was dried overnight in an oven at 60° C. The final catalyst contained 2.11 wt. % Cu and 2.18 wt. % Zn as compared to the total catalyst weight.

The catalyst was calcined in situ prior to the catalytic reaction. The calcination was performed by heating the catalyst to 500° C. in a flow of 10% $O_2$/90% He gas mixture for 3 hours followed by treatment in 10% $H_2$/90% Ar at 500° C. for 2 hours.

The catalyst then was tested in a reaction mixture of 93% CO/2% DME/5% He at 15 mL/min (STP), 0.3 g of total catalyst at 10 bar total pressure and temperature starting at 200° C. and an inert-exclusive WHSV (STP) of 3.6 $h^{-1}$. Temperature was increased during reaction to a final temperature of 420° C.

This catalyst showed no activity for DME carbonylation at any of the temperatures tested, indicating that the zeolite is necessary for the activation of reactant(s).

Example 16. Production and Testing of a Fe(II)/$NH_4$-MOR Catalyst

The $NH_4$-MOR material was produced as described in Example 1. The $NH_4$-MOR was mixed physically with hydrated $FeCl_2$ so as to achieve a 100% loading of Fe(II)

relative to total Al content in the NH₄-MOR. This physical mixture was ground together using a mortar and pestle until homogeneity was achieved and then heated in a packed bed reactor under flowing dry air to 600° C. to facilitate an oxidative solid state ion exchange. The mixture was left at 600° C. under flowing air for a period of 6 hours. The catalyst was retrieved and stored in a desiccator until it was used for carbonylation of DME. The loading of Fe(II) achieved was 3.45 wt. %, which is approximately 72% loading of Fe(II) relative to total Al content on a molar basis.

The catalyst was calcined following the procedure as described in Example 2. The catalyst was reduced in situ at a temperature of 325° C. in 10% $H_2/Ar$ for a period of 2 hours. After this reduction the flow was switched to He and the catalyst was returned to ambient temperature, followed by the catalytic test.

Figure 19:
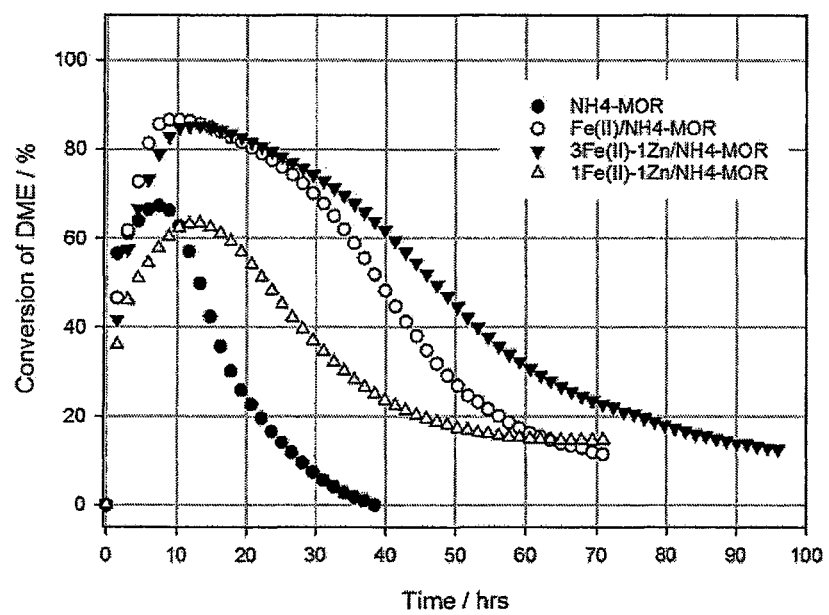
FIG. 19 is a graph showing the conversion of dimethyl ether over time on stream for $NH_4$-MOR, Fe(II)/$NH_4$-MOR (Example 16), 3Fe(II)-1 Zn/$NH_4$-MOR (Example 17), and 1Fe(II)-1Zn/$NR_4$-MOR (Example 18) catalysts. 50.0% CO/2.39% DME/2.86% $H_2$/44.75% He, 15 mL/min (STP), 0.3 g of catalyst, 20 bar, 210° C., inert-exclusive WHSV (STP) of 2.1 $h^{-1}$.
Figure 20:
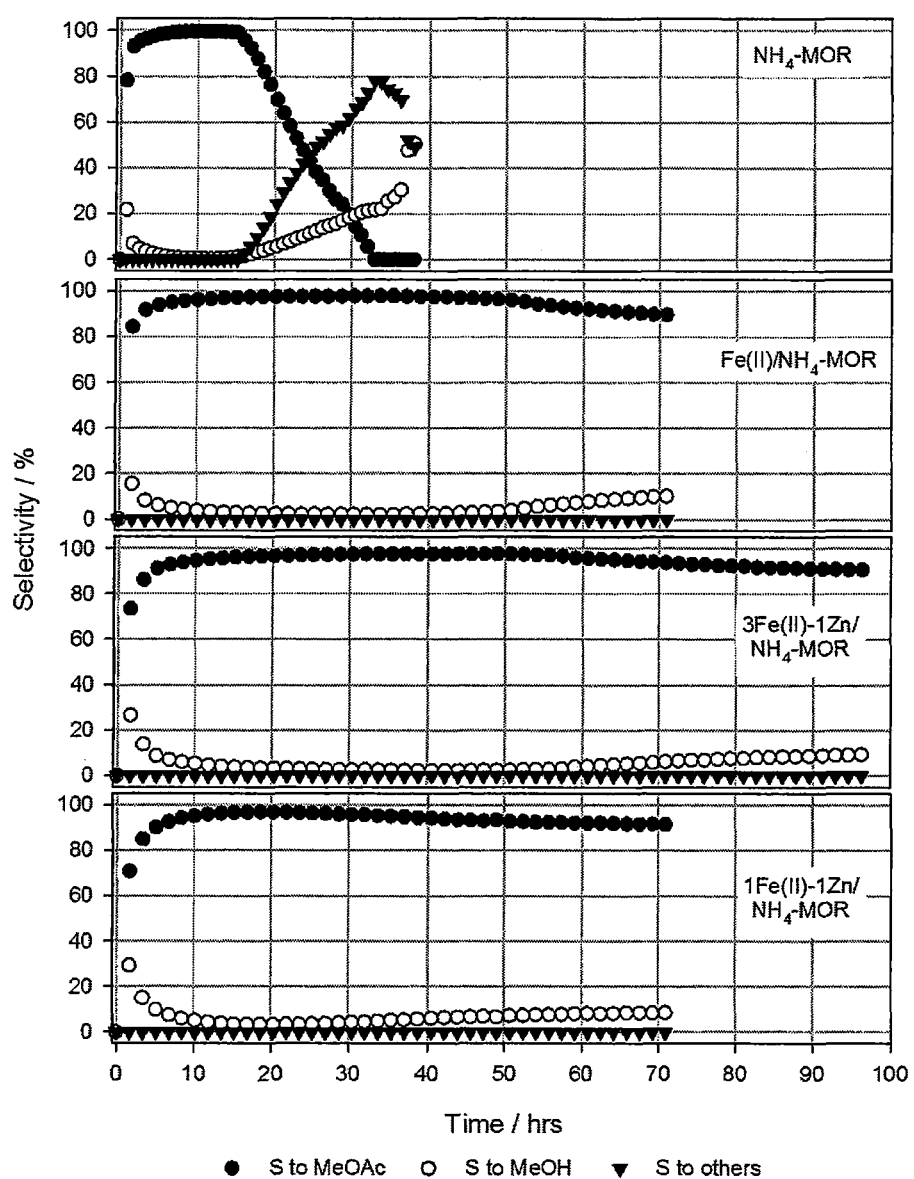
FIG. 20 is a graph showing the selectivity towards methyl acetate, methanol, and to other oxygenates and hydrocarbons over time on stream for the catalysts and reactions in FIG. 19.
Figure 21:
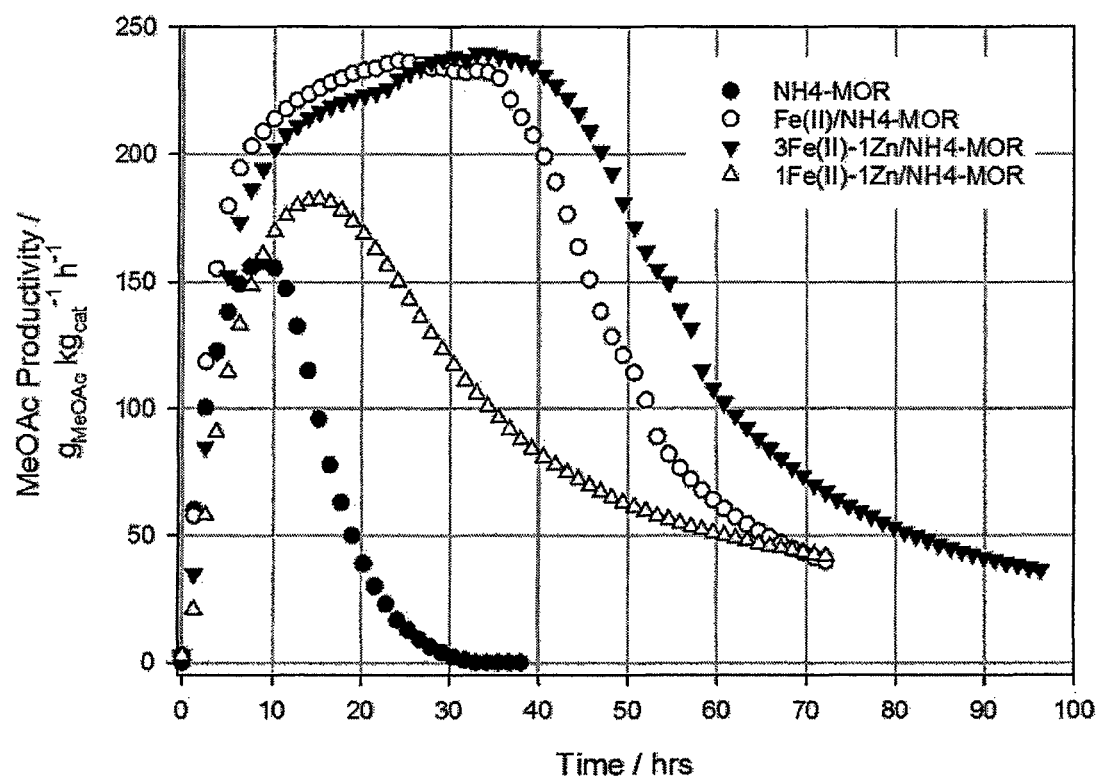
FIG. 21 is a graph showing the methyl acetate productivity for the catalysts and reactions in FIG. 19.

The catalyst was tested in a reaction mixture of 50.0% CO/2.39% DME/2.86% $H_2$/44.75% He at 15 mL/min (STP), 0.3 g of catalyst at 20 bar total pressure at 210° C., and an inert-exclusive WHSV (STP) of 2.1 $h^{-1}$. The results for the reaction are shown in FIGS. 19-21. As compared to NH₄-MOR, substantially higher conversion is achieved despite that the conversion does not achieve a steady state. As was seen with the Cu—Zn/NH₄-MOR catalysts, the selectivity to methyl acetate (MeOAc) is stabilized even as the catalyst begins to deactivate with the main by-product being methanol (MeOH). No other hydrocarbons were detected. MeOAc productivity achieved a relatively stable level for a period of approximately 25 hours before it began to decrease as the catalyst deactivated.

Example 17. Production and Testing of a 3Fe(II)-1 Zn/NH₄-MOR Catalyst

The NH₄-MOR material was produced as described in Example 1. The NH₄-MOR was mixed physically with hydrated $FeCl_2$ and $ZnCl_2$ so as to achieve a 100% loading of Fe and Zn relative to total Al content in the NH₄-MOR and a molar ratio of Fe:Zn of 3.1. The solid state ion exchange was conducted as described in Example 16. The loading of Fe(II) and Zn achieved was 3.00 wt. % and 1.2 wt. %, respectively, which is an approximate 83% loading of Fe(II) and Zn relative to Al content on a molar basis.

The catalyst was calcined and reduced as described in Example 16.

The catalyst was tested for DME carbonylation as described in Example 16. The results for the reaction are shown in FIGS. 19 to 21. As compared to Fe(II)/NH₄-MOR, a slightly lower conversion of DME is achieved but stays at a higher level for longer. Selectivity to MeOAc is slightly better over the entirety of the reaction as compared with the Fe(II)/NR₄-MOR and remains high as the catalyst deactivates. Aside from MeOH, no other hydrocarbons were detected. MeOAc productivity achieved a relatively stable level for a period of approximately 30 hours and was slightly higher as compared to Fe(II)/NH₄-MOR.

Example 18. Production and Testing of a 1 Fe(II)-1 Zn/NH₄-MOR Catalyst

The NH₄-MOR material was produced as described in Example 1. The NH₄-MOR was mixed physically with hydrated $FeCl_2$ and $ZnCl_2$ so as to achieve a 100% loading of Fe and Zn relative to total Al content in the NH₄-MOR and a molar ratio of Fe:Zn of 1.1. The solid state ion exchange was conducted as described in Example 16. The loading of Fe(II) and Zn achieved was 1.90 wt. % and 2.40 wt. %, respectively, which is an approximate 82% loading of Fe(II) and Zn relative to Al content on a molar basis.

The catalyst was calcined and reduced as described in Example 16.

The catalyst was tested for DME carbonylation as described in Example 16. The results for the reaction are shown in FIGS. 19 to 21. As compared to Fe(II)/NH₄-MOR, a much lower conversion of DME is achieved but still higher than NH₄-MOR. Selectivity to MeOAc is not as high over the entirety of the reaction as compared with the 3Fe(II)/NH₄-MOR but does remain in favor of MeOAc with the only by-product detected being MeOH.

Example 19. Production and Testing of H-MOR Catalyst with a Si/Al Ratio of 6.5

The NH₄-MOR material was produced as described in Example 1.

The catalyst was calcined in situ to H-MOR via stepwise increases in temperature. Under a 10% $O_2$/90% He gas mixture, the catalyst was heated to 110° C. for 3 hours, 350° C. for 1.5 hours, and 550° C. for 3 hours. The temperature then was decreased to 325° C., active gas flow switched to pure He, and the temperature was decreased further to ambient temperature. The H-MOR contains 5.1 wt. % Al.

Figure 22:
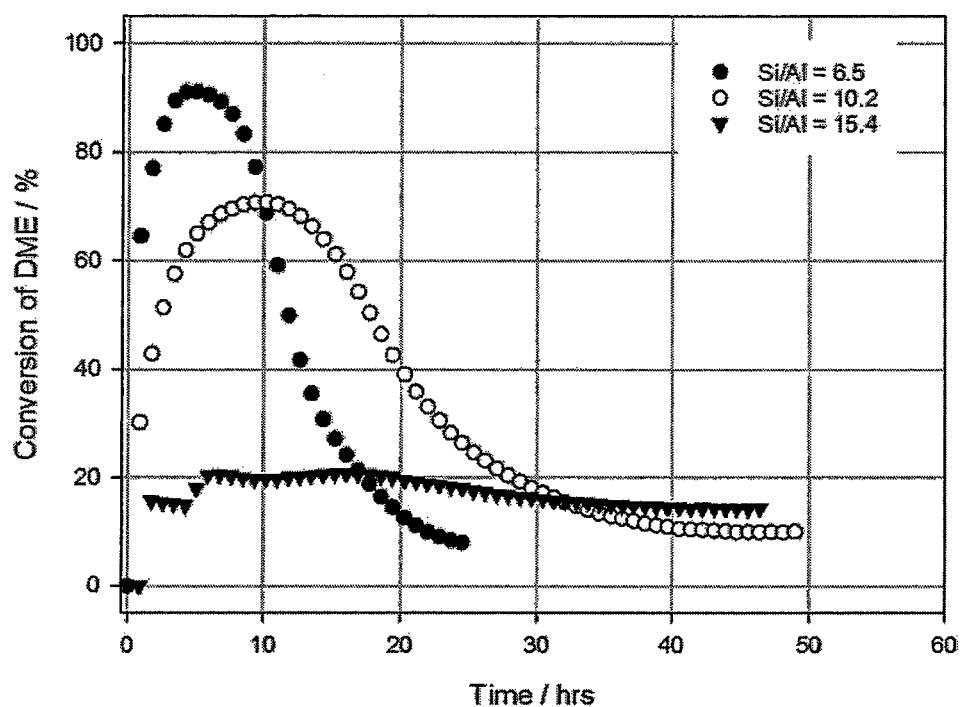
FIG. 22 is a graph showing the conversion of dimethyl ether over time on stream for H-MOR with a Si/Al ratio of 6.5 (Example 19), hierarchical H-MOR with a Si/Al ratio of 10.2 (Example 20), and hierarchical H-MOR with a Si/Al ratio of 15.4 (Example 21). 50.0% CO/2.39% DME/2.86% $H_2$/44.75% He at 15 mL/min (STP), 0.2 g (Example 19), 0.3 g (Example 20), or 0.468 g (Example 21) of catalyst, 20 bar, 210° C.
Figure 23:
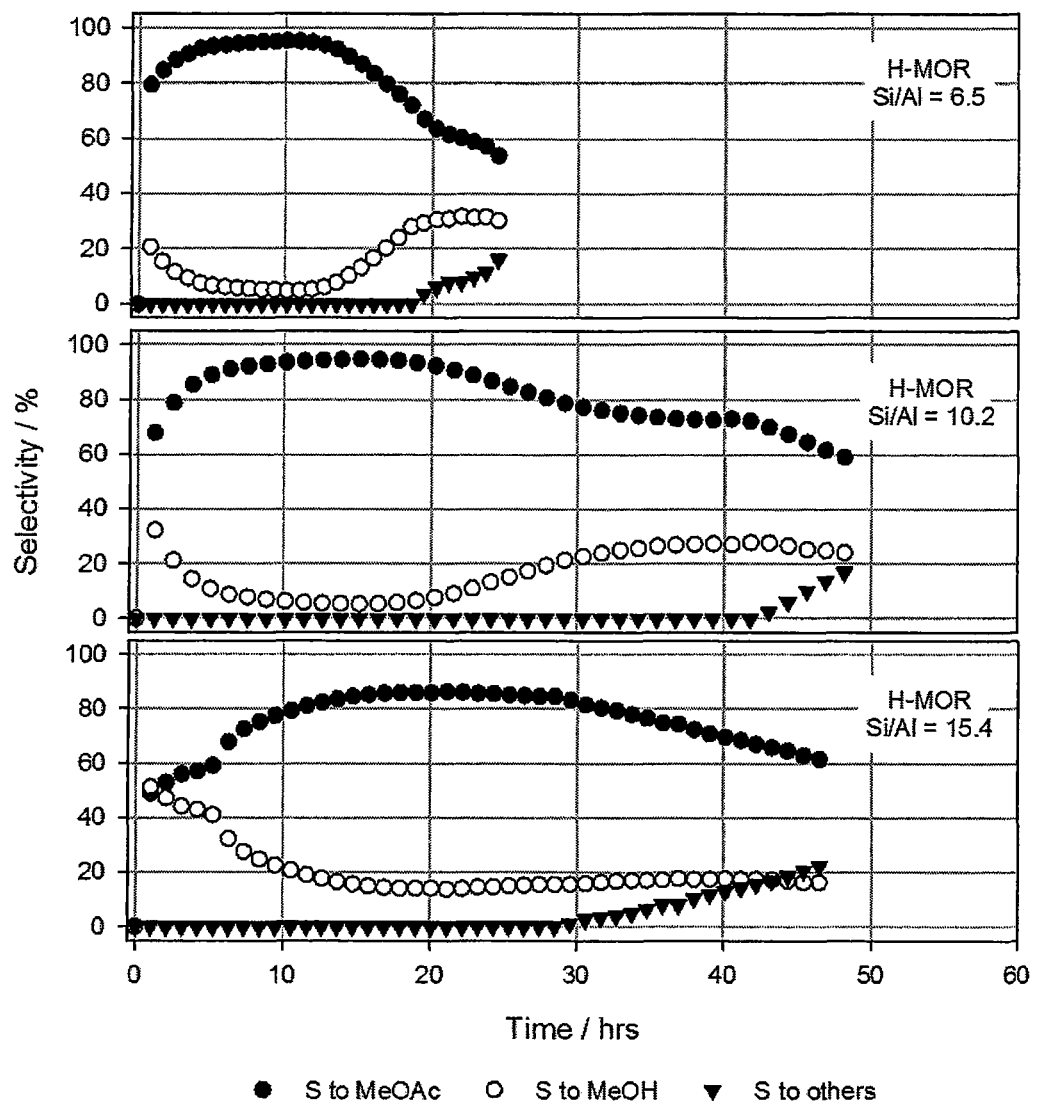
FIG. 23 is a graph showing the selectivity toward methyl acetate, methanol, and to other oxygenates and hydrocarbons over time on stream for the catalysts and reactions in FIG. 22.
Figure 24:
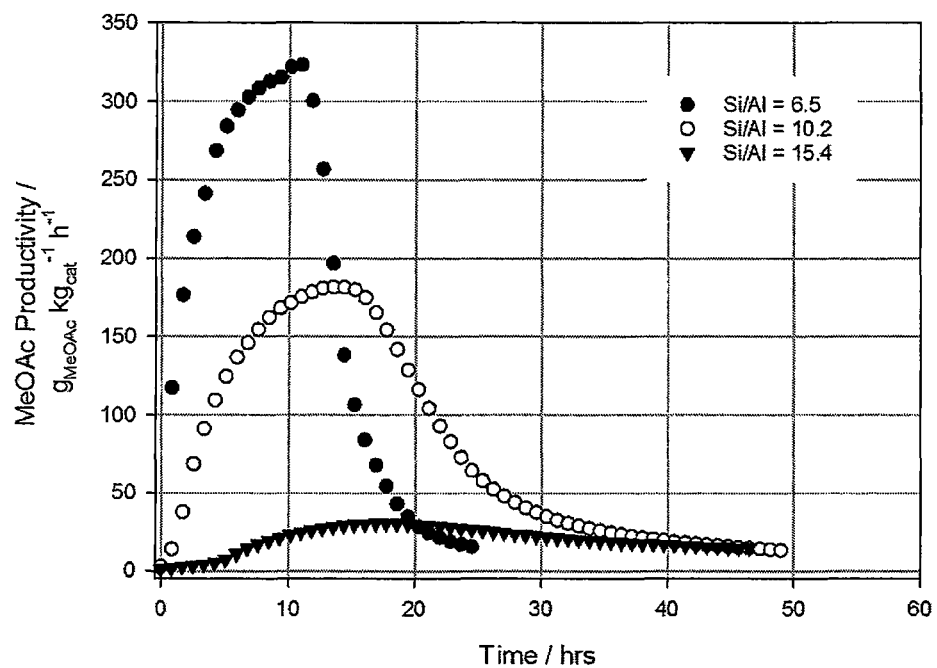
FIG. 24 is a graph showing the methyl acetate productivity for the catalysts and reactions in FIG. 22.

The catalyst was tested in a reaction mixture of 50.0% CO/2.39% DME/2.86% $H_2$/44.75% He at 15 mL/min (STP), 0.2 g of catalyst at 20 bar total pressure at 210° C., and an inert-exclusive WHSV (STP) of 3.09 $h^{-1}$. The results for the reaction are shown in FIGS. 22 to 24. As was seen in Example 1, metal-free H-MOR does not survive very long in reaction, and selectivity to MeOAc decreases as the catalyst deactivates.

Example 20. Production and Testing of Hierarchical H-MOR with a Si/Al Ratio of 10.2

The NH₄-MOR material was produced as described in Example 1. The NH₄-MOR then was mixed with 5 M $HNO_3$ at 50° C. at a ratio of 1 g of NH₄-MOR to 50 mL of solution. The mixture was covered and stirred for one hour using a magnetic stir bar. The mixture then was vacuum filtrated to recover the solids and washed excessively with deionized water. The recovered powder was dried overnight at 60° C.

The catalyst was calcined and prepared for reaction as described in Example 19.

The catalyst was tested for DME carbonylation as described in Example 19 with the only difference being the amount of catalyst used. To maintain approximately the same amount of Al in the reactor as in Example 19, the amount of catalyst used was increased to 0.3 g which gives an inert-exclusive WHSV of 2.1 $h^{-1}$ (catalyst contained approximately 3.4 wt. % Al).

The results for the reaction are shown in FIGS. 22 to 24. As compared to H-MOR with a Si/Al ratio of 6.5, the catalyst is slightly more stable at the cost of reduced activity. The same decrease in selectivity to MeOAc as seen with H-MOR with a Si/Al ratio of 6.5 was seen as the catalyst deactivates.

Example 21. Production and Testing of Hierarchical H-MOR with a Si/Al Ratio of 15.4

To produce Na-MOR with a Si/Al ratio of 15.4, 3 g of Na-MOR with a Si/Al ratio of 6.5 was mixed with 50 mL of 0.55 M $HNO_3$ and heated subsequently under reflux to the point that the mixture was beginning to boil. The mixture was stirred and left boiling for a period of one hour before it was cooled quickly and filtered to recover the solids. The recovered powder was washed excessively with deionized water. The recovered powder then was converted to $NH_4$-MOR as described in Example 1.

The catalyst was calcined and prepared for reaction as described in Example 19.

The catalyst was tested for carbonylation of dimethyl ether as described in Example 19 with the difference being the amount of catalyst used. To keep the Al content in the reactor approximately constant, 0.468 g of hierarchical $NH_4$-MOR was used which gave an inert-exclusive WHSV of 1.32 $h^{-1}$ (catalyst contained approximately 2.35 wt. % Al). The results for the reaction are shown in FIGS. 22 to 24. As compared to H-MORs with Si/Al ratios of 6.5 and 10.2, activity is decreased significantly and peak conversion is approximately 20%. Selectivity to MeOAc also is lower with selectivity to MeOH increased from what was seen at the ratios tested in Examples 19 and 20. MeOAc productivity is significantly less with peak productivity around 30 $g_{MeOAc}$ $kg_{cat}^{-1}$ $h^{-1}$.

Example 22. Production and Testing of Hierarchical H/MOR with a Si/Al Ratio of 7.7

To produce Na-MOR with a Si/Al ratio of 7.7, 3 g of Na-MOR with a Si/Al ratio of 6.5 was mixed with 50 mL of 0.08 M $HNO_3$ and heated subsequently to approximately 50° C. The mixture was stirred and left boiling for a period of one hour before it was cooled and filtered quickly to recover the solids. The recovered powder was washed excessively with deionized water. The recovered powder then was converted to $NH_4$-MOR as described in Example 1.

The catalyst was calcined and prepared for reaction as described in Example 19.

Figure 25:
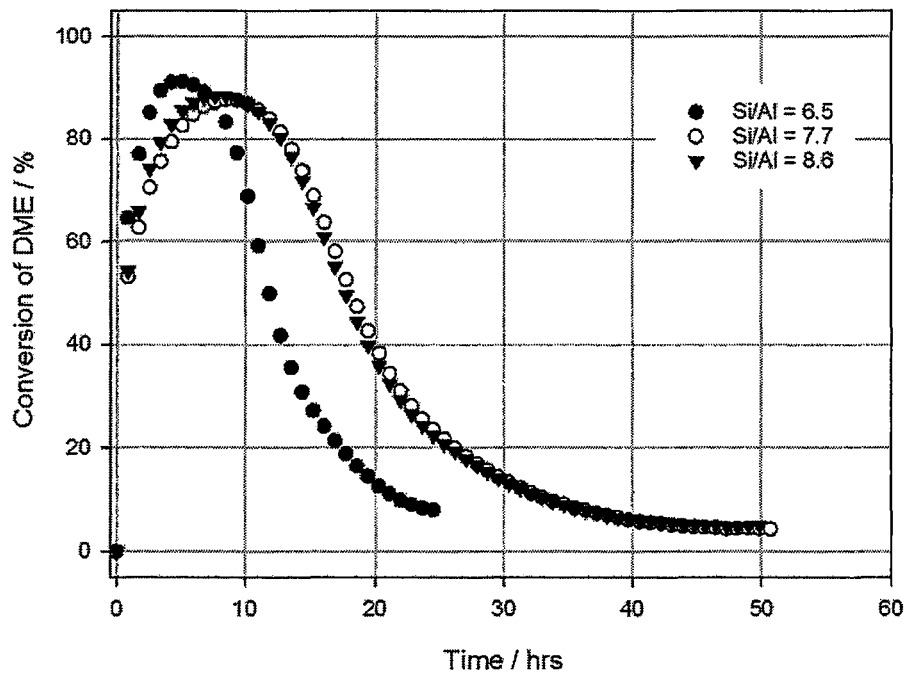
FIG. 25 is a graph showing the conversion of dimethyl ether over time on stream for H-MOR with a Si/Al ratio of 6.5 (Example 19), hierarchical H-MOR with a Si/Al ratio of 7.7 (Example 22), and hierarchical H-MOR with a Si/Al ratio of 8.6 (Example 23). 50.0% CO/2.39% DME/2.86% $H_2$/44.75% He at 15 mL/min (STP), 0.2 g (Example 19), 0.232 g (Example 22), and 0.254 g (Example 23) of catalyst, 20 bar, 210° C.
Figure 26:
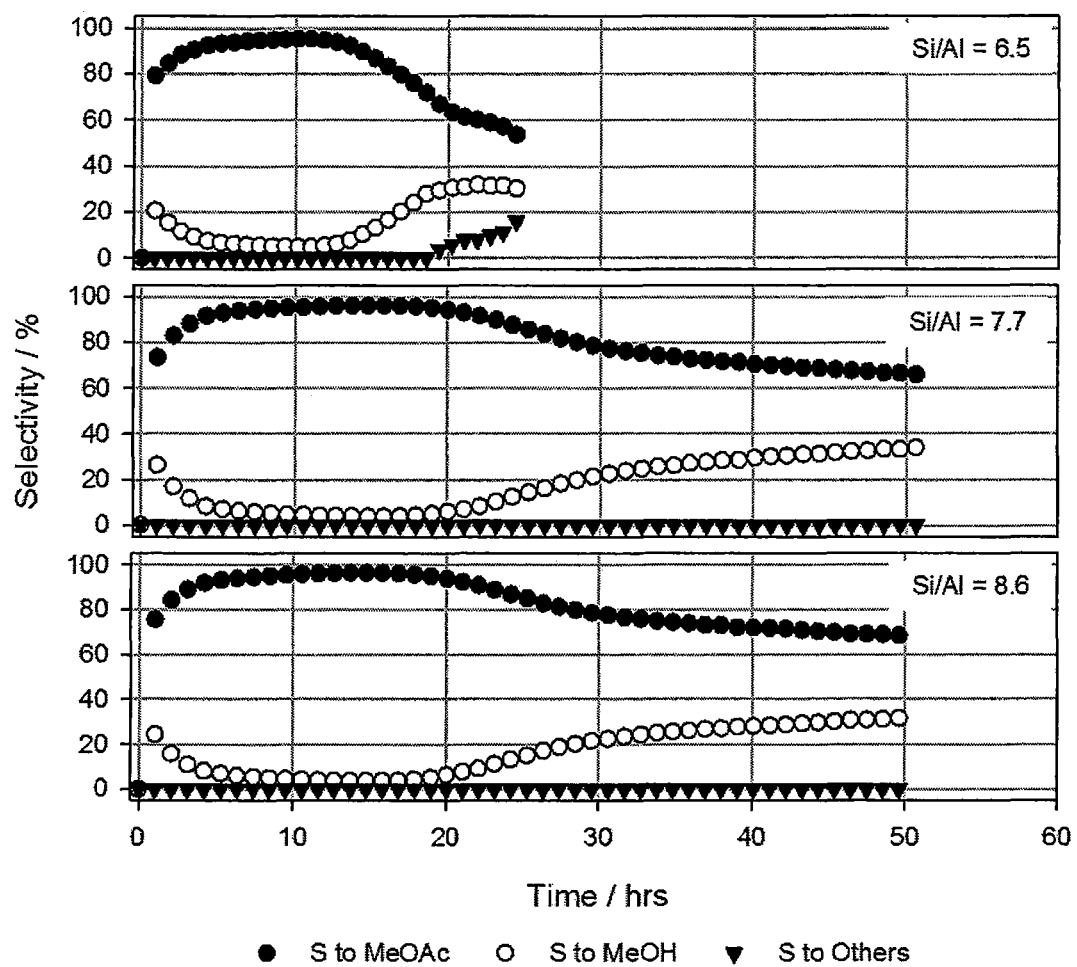
FIG. 26 is a graph showing the selectivity toward methyl acetate, methanol, and to other oxygenates and hydrocarbons over time on stream for the catalyst and reactions in FIG. 25.
Figure 27:
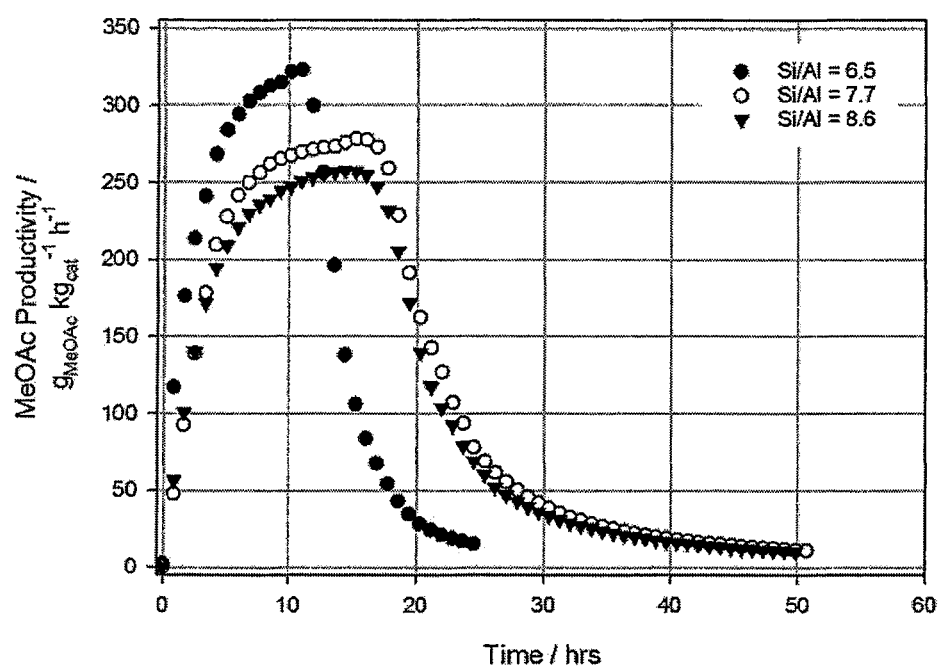
FIG. 27 is a graph showing the methyl acetate productivity for the catalysts and reactions in FIG. 25.

The catalyst was tested for DME carbonylation as described in Example 19 with the only difference being the amount of catalyst used. To maintain approximately the same amount of Al in the reactor as in Example 19, the amount of catalyst used was increased to 0.232 g which gives an inert-exclusive WHSV of 2.66 $H^{-1}$. The H-MOR contains 4.4 wt % Al. The results for the reaction are shown in FIGS. 25 to 27 compared against the results of H/MOR with a Si/Al ratio of 6.5 as described in Example 19. As compared to H/MOR with a Si/Al ratio of 6.5, peak conversion is slightly less with a Si/Al ratio of 7.7, but the reaction time is double that of H/MOR with a Si/Al ratio of 6.5. This leads to a substantially higher amount of MeOAc produced per unit of Al at no loss in selectivity as shown in FIGS. 26 and 27.

Example 23. Production and Testing of Hierarchical H-MOR with a Si/Al Ratio of 8.6

To produce a Na-MOR with a Si/Al ratio of 8.6, 3 g of Na-MOR with a Si/Al ratio of 6.5 was mixed with 50 mL of 0.139 M $HNO_3$ and heated subsequently to approximately 50° C. The mixture was stirred and left boiling for a period of one hour before it was cooled and filtered quickly to recover the solids. The recovered powder was washed excessively with deionized water. The recovered powder then was converted to $NH_4$-MOR as described in Example 1.

The catalyst was calcined and prepared for reaction as described in Example 19.

The catalyst was tested for DME carbonylation as described in Example 19 with the only difference being the amount of catalyst used. To maintain approximately the same amount of Al in the reactor as in Example 19, the amount of catalyst used was increased to 0.254 g which gives an inert-exclusive WHSV of 2.43 $H^{-1}$. The H-MOR contains 4.0 wt. % Al. The results for the reaction are shown in FIGS. 25 to 27. As compared to H-MOR with a Si/Al ratio of 7.7, the results were similar.

Example 24. Production and Testing of 1Cu-4Zn/$NH_4$-MOR Catalyst

The $NH_4$-MOR material was produced as described in Example 1. It was ion-exchanged further using 0.021 M $Cu(NO_3)_2$ and 0.179M $Zn(NO_3)_2$ aqueous solutions; the ion exchange was repeated 4 times to achieve an approximate molar ratio of 1:4 Cu:Zn and metal loading of 0.58 wt. % Cu and 2.50 wt. % Zn. In the time between the final ion exchange and being used in the carbonylation reaction, this catalyst was stored in a furnace maintained at 60° C.

The catalyst was calcined following the procedure as described in Example 2. The catalyst was reduced in situ at a temperature of 325° C. in 10% $H_2$/Ar for a period of 2 hours. After this reduction the flow was switched to He and the catalyst was returned to ambient temperature, followed by the catalytic test.

Figure 28:
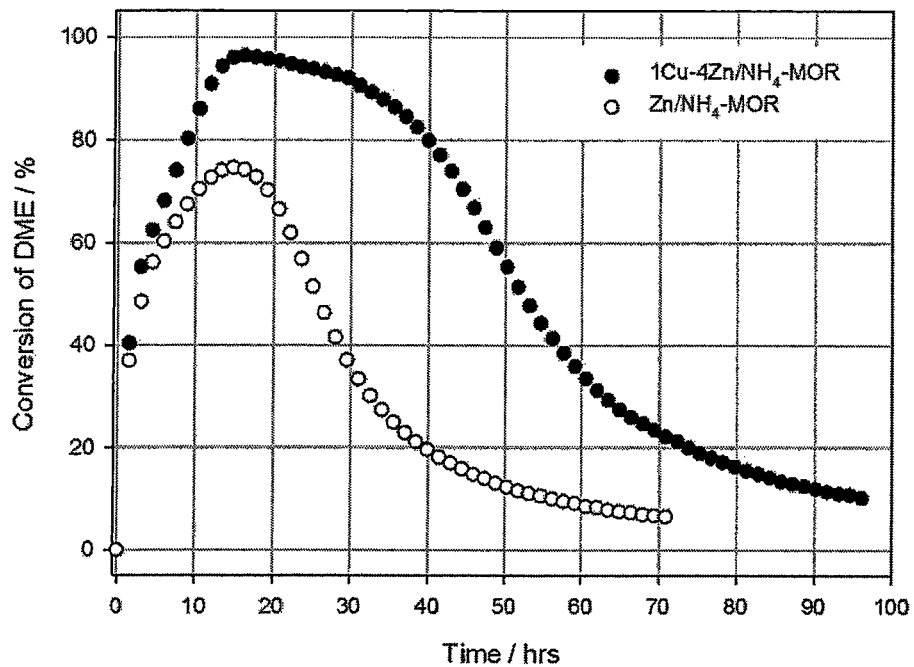
FIG. 28 is a graph showing the conversion of dimethyl ether over time on stream for 1Cu-4Zn/NH$_4$-MOR (Example 24) and Zn/NH$_4$-MOR (Example 25). 50.0% CO/2.39% DME/2.86% H$_2$/44.75% He, 15 mL/min (STP), 0.3 g of catalyst, 20 bar, 210° C., inert-exclusive WHSV (STP) of 2.1 h$^{-1}$.
Figure 29:
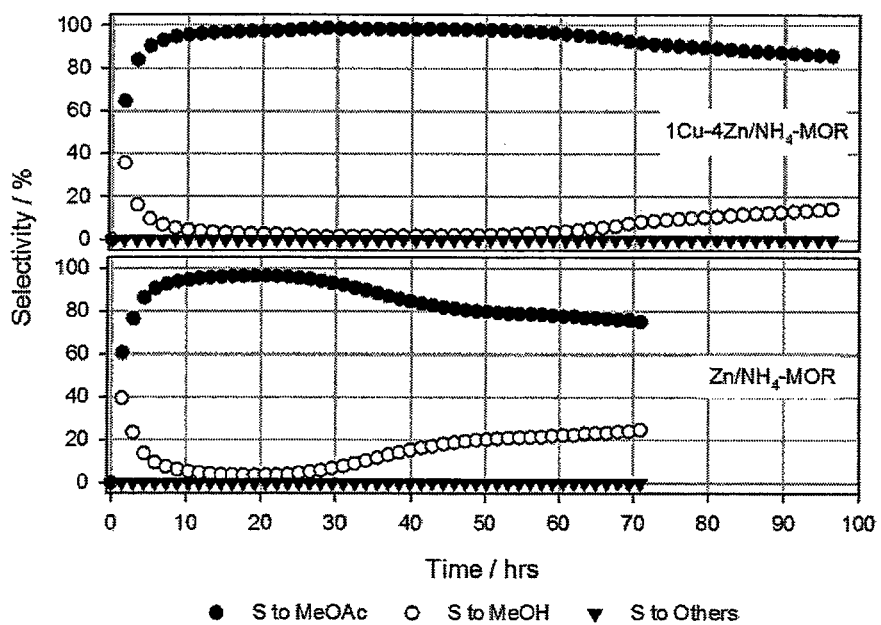
FIG. 29 is a graph showing the selectivity towards methyl acetate, methanol, and to other oxygenates and hydrocarbons over time on stream for the catalysts and reactions in FIG. 28.
Figure 30:
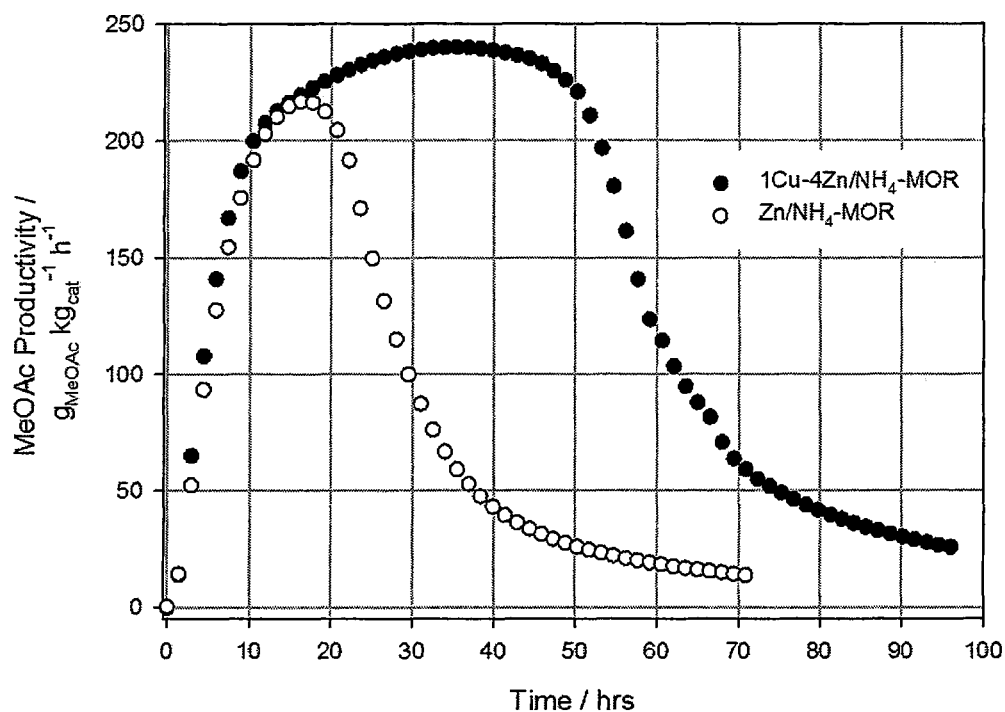
FIG. 30 is a graph showing the methyl acetate productivity for the catalysts and reactions in FIG. 28.

The catalyst was tested for DME carbonylation as described in Example 16. The results for the reaction are shown in FIGS. 28 to 30. As compared to the 1Cu-3.5Zn/$NH_4$-MOR catalyst described in Example 5, the stability is improved slightly showing increased conversion of DME. The MeOAc productivity is improved significantly both in terms of stability and peak productivity (240 $g_{MeOAc}$ $kg_{cat}^{-1}$ $h^{-1}$ vs. 200 $g_{MeOAc}$ $kg_{cat}^{-1}$ $h^{-1}$). The selectivity towards MeOAc is nearly 100% for the majority of the reaction, decreasing slightly as the catalyst deactivates with the only other by-product detected being MeOH.

Example 25. Production and Testing of Zn/$NH_4$-MOR Catalyst

The $NH_4$-MOR material was produced as described in Example 1. It was ion-exchanged further using a 0.2 M $Zn(NO_3)_2$ aqueous solution; the ion exchange was repeated 4 times to achieve an approximate metal loading 3.05 wt. % Zn.

The catalyst was calcined following the procedure as described in Example 2. The catalyst was reduced in situ at a temperature of 325° C. in 10% $H_2$/Ar for a period of 2 hours. After this reduction the flow was switched to He and the catalyst was returned to ambient temperature, followed by the catalytic test.

The catalyst was tested for DME carbonylation as described in Example 16. The results for the reaction are shown in FIGS. 28 to 30. As compared to the Cu/$NH_4$-MOR catalyst described in Example 2, the stability is improved significantly but does not achieve the same peak DME conversion. A slightly higher peak MeOAc productivity is achieved as well and selectivity also is enhanced greatly with the only other by-product detected being MeOH. As compared to the 1Cu-4Zn/$NH_4$-MOR, however, the overall conversion and MeOAc productivity is decreased substantially as shown in FIGS. 28 to 30. The benefit of the bimetallic catalyst is apparent.

Example 26. Production and Testing of Hierarchical 3Fe-1Zn/$NH_4$-MOR with a Ratio Si/Al Ratio of 8.6

The hierarchical $NH_4$-MOR material with a Si/Al ratio of 8.6 was produced as described in Example 23. The hierarchical NH$_4$-MOR with a Si/Al ratio of 8.6 was mixed physically with hydrated FeCl$_2$ and ZnCl$_2$ so as to achieve a 100% loading of Fe and Zn relative to total Al content in the NH$_4$-MOR and a molar ratio of Fe:Zn of 3.1. The solid state ion exchange was conducted as described in Example 16. The loading of Fe(II) and Zn achieved was 2.40 wt. % and 0.94 wt. %, respectively, which is an approximate 80% loading of Fe(II) and Zn relative to Al content on a molar basis.

The catalyst was calcined in situ prior to the catalytic reaction. The calcination was performed stepwise in a 10% O$_2$/90% He gas mixture to avoid sieve damage by steaming at 110° C. for 3 hours, 350° C. for 1.5 hours, and 550° C. for 3 hours. After calcination the catalyst was reduced in a 10% H$_2$/90% Ar gas mixture at 325° C. for two hours. After these treatments the catalyst was stored under He.

Figure 31:
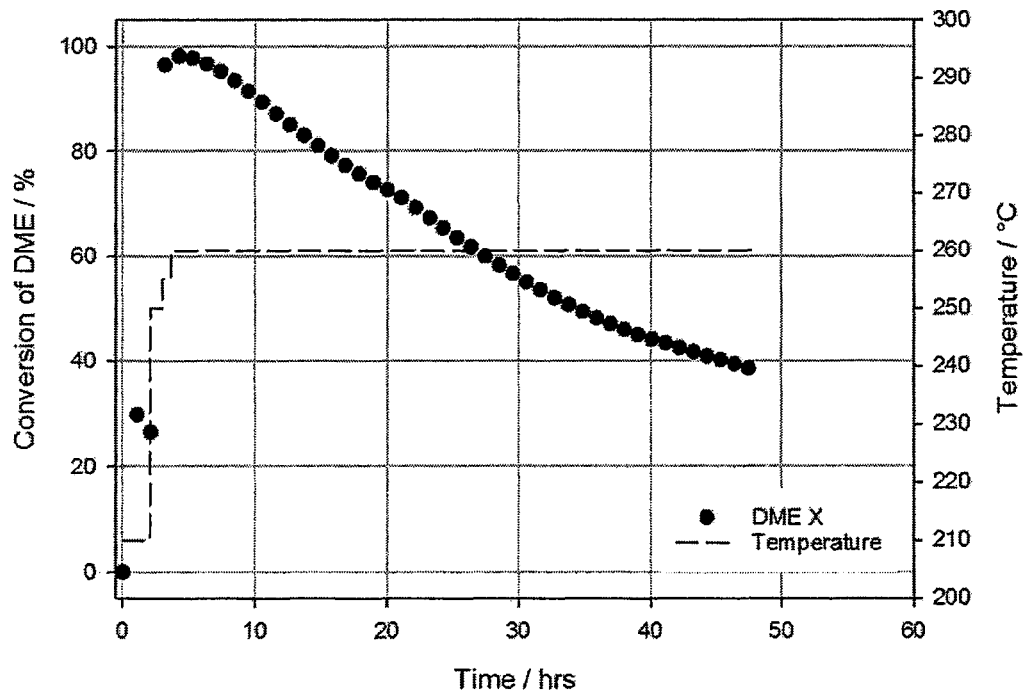
FIG. 31 is a graph showing the conversion of dimethyl ether over time on stream for hierarchical 3Fe-1Zn/NH$_4$-MOR with a Si/Al ratio of 8.6 (Example 26), 93% CO/2% DME/5% He, 15 mL/min (STP), 0.0.15 g of catalyst, 20 bar, 210° C., inert-exclusive WHSV (STP) of 7.2 h$^{-1}$.
Figure 32:
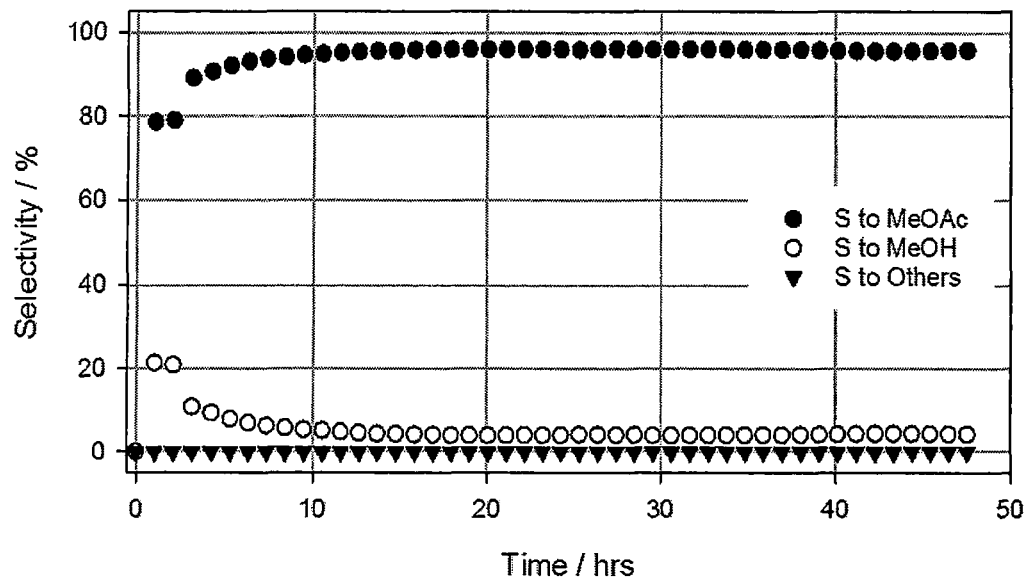
FIG. 32 is a graph showing the selectivity towards methyl acetate, methanol, and to other oxygenates and hydrocarbons over time on stream for the catalyst and reaction in FIG. 31.
Figure 33:
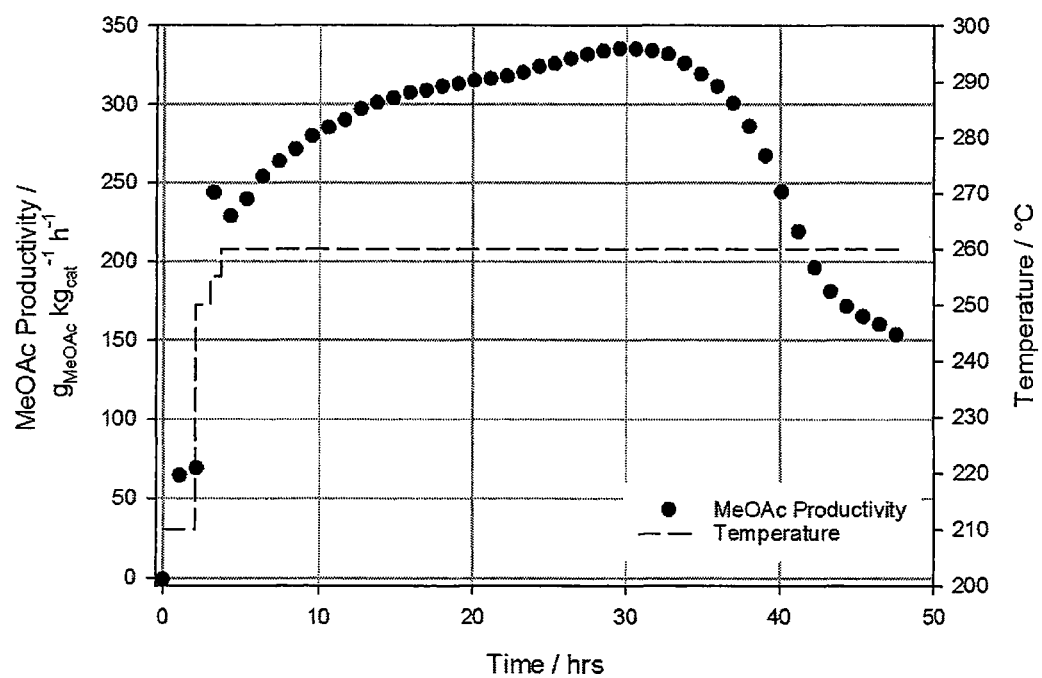
FIG. 33 is a graph showing the methyl acetate productivity for the catalyst and reaction in FIG. 31.

The catalyst then was tested in a reaction mixture of 93% CO/2% DME/5% He at 15 mL/min (STP), 0.15 g of a catalyst at 20 bar total pressure and starting at 210° C., and an inert-exclusive WHSV (STP) of 7.2 h$^{-1}$. The results for the reaction are shown in FIGS. 31-33. The initial temperature of 210° C. was not sufficient to facilitate the reaction and a final temperature of 260° C. was used as shown in FIGS. 31 and 33. Selectivity during the entirety of reaction was constant with selectivity towards MeOAc being approximately 96%. Conversion of DME decreased at a constant rate during the entirety of the reaction. A peak MeOAc productivity of approximately 340 $g_{MeOAc}$ $kg_{cat}^{-1}$ h$^{-1}$ was achieved which was substantially higher than any other catalyst tested.

The disclosure of all patents and publications (including published patent applications) are incorporated herein by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A catalyst for the carbonylation of dimethyl ether to produce methyl acetate, comprising: (i) a mordenite zeolite; (ii) zinc; and (iii) copper, wherein said copper and said zinc are present in said catalyst at a molar ratio of said copper to said zinc of about 0.25.

2. The catalyst of claim 1 wherein said catalyst is free of halogens and halogen-containing compounds.

3. The catalyst of claim 1, and further comprising: (iv) palladium.

4. The catalyst of claim 1 wherein said mordenite zeolite has a Si/Al ratio of from about 5:1 to about 90:1.

5. The catalyst of claim 4 wherein said mordenite zeolite has a Si/Al ratio of from about 5:1 to about 50:1.

* * * * *